US006171794B1

(12) United States Patent
Burchard et al.

(10) Patent No.: US 6,171,794 B1
(45) Date of Patent: Jan. 9, 2001

(54) METHODS FOR DETERMINING CROSS-HYBRIDIZATION

(75) Inventors: Julja Burchard, Kirkland, WA (US); Roland Stoughton, San Diego, CA (US); Stephen H. Friend, Seattle, WA (US)

(73) Assignee: Rosetta Inpharmatics, Inc., Kirkland, WA (US)

( * ) Notice: Under 35 U.S.C. 154(b), the term of this patent shall be extended for 0 days.

(21) Appl. No.: 09/335,971

(22) Filed: Jun. 18, 1999

Related U.S. Application Data

(60) Provisional application No. 60/092,512, filed on Jul. 13, 1998.

(51) Int. Cl.[7] .............................. C12Q 1/68; C12M 1/34; C07H 21/07

(52) U.S. Cl. ......................... 435/6; 435/287.2; 536/23.1; 536/24.31

(58) Field of Search .............................. 435/6, 6.6, 287.1; 536/23.1, 24.31

(56) References Cited

U.S. PATENT DOCUMENTS

| | | |
|---|---|---|
| 5,510,270 | 4/1996 | Fodor et al. . |
| 5,539,082 | 7/1996 | Nielsen et al. . |
| 5,539,083 | 7/1996 | Cook et al. . |
| 5,556,752 | 9/1996 | Lockhart et al. . |
| 5,569,588 | 10/1996 | Ashby et al. . |
| 5,578,832 | 11/1996 | Trulson et al. . |
| 5,599,668 | 2/1997 | Stimpson et al. . |

FOREIGN PATENT DOCUMENTS

| | | |
|---|---|---|
| WO 98/12354 | 3/1998 | (WO) . |
| WO 98/41531 | 9/1998 | (WO) . |

OTHER PUBLICATIONS

Bernard et al. (1998) "Integrated Amplification and Detection of the C677T Point Mutation in the Methylenetetrahydrofolate Reductase Gene by Fluorescence Resonance Energy Transfer and Probe Melting Curves," Analytical Biochem. 255:101–107.

Phillips et al. (1989) "O(log n) Bimodality Analysis," Pattern Recognition 22(6):741–746.

Wallace et al. (1979) "Hybridization of Synthetic Oligodeoxyribonucleotides to $\phi_X$ 174 DNA: The Effect of Single Base Pair Mismatch," Nucleic Acids Research 6(11):3543–3557.

Anshelevich et al., 1984, "Slow relaxation processes in the melting of linear biopolymers: a theory and its application to nucleic acids", Biopolymers 23:39–58.

Blake, 1995, "Denaturation of DNA", *Molecular Biology and Biotechnology* (VCH Publishers, Cambridge) pp. 207–210.

National Center for Biotechnology Information, 1994, "NCBI creates new database, new GenBank division for STS data", NCBI News. Feb.; 3(1):2.

*Primary Examiner*—Stephanie W. Zitomer
(74) *Attorney, Agent, or Firm*—Pennie & Edmonds LLP

(57) ABSTRACT

The present invention provides methods for distinguishing the fractions of polynucleotide sequences which hybridize to any given probe, including probes on microarrays such as those described herein. In particular, the present invention enables users to identify the fraction of sequences which are perfectly complementary to a probe, thereby correcting for effects of cross hybridization in a hybridization assay. The methods of the invention work by monitoring the kinetics of dissociation of sequences from the probe so that a resulting "dissociation curve" may be compared to a combination of the individual "dissociation profiles" for each sequence which hybridizes. In alternative embodiments, the invention also provides computer systems for performing the present methods, as well as databases of the dissociation profiles.

75 Claims, 8 Drawing Sheets

OTHER PUBLICATIONS

Olson M et al., 1989, "A common language for physical mapping of the human genome", Science. Sep. 29;245(4925):1434–5.

Wetmur, 1995, "Nucleic acid hydribs", *Molecular Biology and Biotechnology* (VCH Publishers, Cambridge) pp. 605–607.

Albretsen et al., 1988, "Optimal conditions for hybridization with oligonucleotides: a study with myc–oncogene DNA probes", Anal Biochem 170:193–202.

Ausubel et al., eds., 1989, Current Protocols in Molecular Biology, vol. I, Green Publishing Associates, Inc., John Wiley & Sons, Inc., New York, pp. 2.10.1–2.10.16 and 13.12.1–13.12.5.

Beattie et al., 1995, "Hybridization of DNA targets to glass–tethered oligonucleotide probes", Mol Biotechnol 4:213–225.

Blanchard and Hood, 1996, "Sequence to array: probing the genome's secrets", Nat Biotechnol 14:1649.

Blanchard and Hood, 1996, "High–density oligonucleotide arrays", Biosensors and Bioelectronics 11:687–690.

Chirgwin et al., 1979, "Isolation of biologically active ribonucleic acid from sources enriched in ribonuclease", Biochemistry 18:5294–5299.

Day et al., 1995, "Electrophoresis for genotyping: temporal thermal gradient gel electrophoresis for profiling of oligonucleotide dissociation", Nucleic Acids Res 23:2404–2412.

DeRisi et al., 1996, "Use of a cDNA microarray to analyse gene expression patterns in human cancer", Nat Genet 14:457–460.

Egholm et al., 1993, "PNA hybridizes to complementary oligonucleotides obeying the Watson–Crick hydrogen––bonding rules", Nature 365:566–568.

Fodor et al., 1991, "Light–directed, spatially addressable parallel chemical synthesis", Science 251:767–773.

Froehler et al., 1986, "Synthesis of DNA via deoxynucleoside H–phosphonate intermediates", Nucleic Acids Res 14:5399–5407.

Goffeau et al., 1996, "Life with 6000 genes", Science 274:546, 563–567.

Guo et al., 1997, "Enhanced discrimination of single nucleotide polymorphisms by artificial mismatch hybridization", Nat Biotechnol 15:331–335.

Hyndman et al., 1996, "Software to determine optimal oligonucleotide sequences based on hybridization simulation data", Biotechniques 20:1090–1097.

Ikuta et al., 1987, "Dissociation kinetics of 19 base paired oligonucleotide–DNA duplexes containing different single mismatched base pairs", Nucleic Acids Res 15:797–811.

Kajimura et al., 1990, "Application of long synthetic oligonucleotides for gene analysis: effect of probe length and stringency conditions on hybridization specificity", Genet Anal Tech Appl 7:71–79.

Kunitsyn et al., 1996, "Partial thermodynamic parameters for prediction stability and washing behavior of DNA duplexes immobilized on gel matrix", J Biomol Struct Dyn 14:239–244.

Lockhart et al., 1996, "Expression monitoring by hybridization to high–density oligonucleotide arrays", Nat Biotechnol 14:1675–1680.

Maskos and Southern, 1992, "Oligonucleotide hybridizations on glass supports: a novel linker for oligonucleotide synthesis and hybridization properties of oligonucleotides synthesised in situ", Nucleic Acids Res 20:1679–1684.

McBride and Caruthers, 1983, "An investigation of several deoxynucleoside phosphoramidites useful for synthesizing deoxyoligonucleotides", Tetrahedron Lett 24:245–248.

Nguyen et al., 1995, "Differential gene expression in the murine thymus assayed by quantitative hybridization of arrayed cDNA clones", Genomics 29:207–216.

Nicoloso et al., 1989, "Titration of variant DNA sequences differing by a single point–mutation by selective dot–blot hybridization with synthetic oligonucleotides", Biochem Biophys Res Comm 159:1233–1241.

Niemeyer et al., 1998, "Hybridization characteristics of biomolecular adaptors, covalent DNA—streptavidin conjugates", Bioconjug Chem 9:168–175.

Pease et al., 1994, "Light–generated oligonucleotide arrays for rapid DNA sequence analysis", Proc Natl Acad Sci USA 91:5022–5026.

Persson et al., 1997, "Analysis of oligonucleotide probe affinities using surface plasmon resonance: a means for mutational scanning", Anal Biochem 246:34–44.

Sambrook et al., eds., 1989, Molecular Cloning: A Laboratory Manual, 2nd Ed. Cold Spring Harbor Laboratory Press, Cold Spring Harbor, New York, pp. 9.47–9.51 and 11.55–11.61.

SantaLucia, 1988, "A unified view of polymer, dumbbell, and oligonucleotide DNA nearest–neighbor thermodynamics", Proc Natl Acad Sci USA 95:1460–1465.

Schena et al., 1995, "Quantitative monitoring of gene expression patterns with a complementary DNA microarray", Science 270:467–470.

Schena et al., 1996, "Parallel human genome analysis: microarray–based expression monitoring of 1000 genes", Proc Natl Acad Sci USA 93:10614–10619.

Shalon et al., 1996, "A DNA microarray system for analyzing complex DNA samples using two–color fluorescent probe hybridization", Genome Res 6:639–645.

Stimpson et al., 1995, "Real–time detection of DNA hybridization and melting on oligonucleotide arrays by using optical wave guides", Proc Natl Acad Sci USA 92:6379–6383.

Vernier et al., 1996, "Radioimager quantification of oligonucleotide hybridization with DNA immobilized on transfer membrane: application to the identification of related sequences", Anal Biochem 235:11–19.

Wang et al., 1995, "Origins of high sequence selectivity: a stopped–flow kinetics study of DNA/RNA hybridization by duplex– and triplex–forming oligonucleotides", Biochem 34:9774–9784.

Wetmur, 1991, "DNA probes: applications of the principles of nucleic acid hybridization", Crit Rev Biochem Mol Biol 26:227–259.

Young and Wagner, 1991, "Hybridization and dissociation rates of phosphodiester or modified oligodeoxynucleotides with RNA at near–physiological conditions", Nucleic Acids Res 19:2463–2470.

Bernstein, A. et al., Presence & Expression of Friend erythroleukemia . . . Cell Bio. 76(9)4455, 1979.*

Hames B, et al., Nucleic Acid Hybridization:A pratical approach, pp. 76–108, 1985.*

* cited by examiner

METHODS FOR DETERMINING CROSS-HYBRIDIZATION

This application claims benefit under 35 U.S.C. § 119(e) of copending U.S. provisional patent application Ser. No. 60/092,512 filed on Jul. 13, 1998 which is incorporated herein by reference in its entirety.

TABLE OF CONTENTS
1. FIELD OF THE INVENTION
2. BACKGROUND
3. SUMMARY OF THE INVENTION
4. BRIEF DESCRIPTION OF THE DRAWINGS
5. DETAILED DESCRIPTION
   5.1. DETERMINING CROSS HYBRIDIZATION
      5.1.1. DETERMINING HYBRIDIZATION LEVELS
      5.1.2. OBTAINING DISSOCIATION PROFILES
      5.1.3. COMPUTATIONAL METHODS
   5.2. IMPLEMENTATION SYSTEMS AND METHODS
   5.3. MEASUREMENT OF HYBRIDIZATION LEVELS
      5.3.1. MICROARRAYS GENERALLY
      5.3.2. PREPARING PROBES FOR MICROARRAYS
      5.3.3. ATTACHING PROBES TO THE SOLID SURFACE
      5.3.4. TARGET POLYNUCLEOTIDE MOLECULES
      5.3.5. HYBRIDIZATION TO MICROARRAYS
6. EXAMPLES
   6.1. MEASUREMENT OF DISSOCIATION CURVES
   6.2. DETERMINATION OF DISSOCIATION PROFILES
   6.3. FITTING A DISSOCIATION CURVE TO A PERFECT MATCH DISSOCIATION PROFILE
7. REFERENCES CITED

1. FIELD OF THE INVENTION

The field of this invention relates to methods for distinguishing the similarity of nucleic acid sequences by their hybridization properties, and particularly for distinguishing nucleic acid sequences in a sample which are completely complementary to a nucleic acid probe from sequences which are only partially complementary to the probe.

2. BACKGROUND

The ability to distinguish and compare nucleic acid molecules having varying levels of sequence similarity is a matter of great interest to many researchers. Presently, assays involving hybridization of nucleic acid molecules to a complementary probe are the only way to detect the presence of a particular sequence or sequences in a complex sample comprising several different nucleic acid sequences. For example, the nucleic acid sequence similarity of a pair of nucleic acid molecules can be distinguished by allowing the nucleic acid molecules to hybridize, and following the kinetic and equilibrium properties of duplex formation (see, e.g., Sambrook, J. et al., eds., 1989, *Molecular Cloning: A Laboratory Manual,* 2nd Ed., Cold Spring Harbor Laboratory Press, Cold Spring Harbor, N.Y., at pp. 9.47–9.51 and 11.55–11.61; Ausubel et al., eds., 1989, *Current Protocols in Molecular Biology,* Vol I, Green Publishing Associates, Inc., John Wiley & Sons, Inc., New York, at pp. 2.10.1–2.10.16; Wetmur, J. G., 1991, *Critical Reviews in Biochemistry and Molecular Biology* 26:227–259; Persson, B. et al., 1997, *Analytical Biochemistry* 246:34–44; Albretsen, C. et al., 1988, *Analytical Biochemistry* 170:193–202; Kajimura, Y. et al., 1990, *GATA* 7:71–79; Young, S. and Wagner, R. W., 1991, *Nucleic Acids Research* 19:2463–2470; Guo, Z. et al., 1997, *Nature Biotechnology* 15:331–335; Wang, S. et al., 1995, *Biochemistry* 34:9774–9784; Niemeyer, C. M. et al., 1998, *Bioconjugate Chemistry* 9:168–175).

In particular, many assays for detecting nucleic acid sequences in a sample comprise binding a set of nucleic acid probes to a solid support, permitting a labeled nucleic acid species to bind to the immobilized nucleic acid, washing off any unbound material, and detecting the bound, labeled sequence. For example, in blotting assays, such as dot or Southern Blotting, nucleic acid molecules may be first separated, e.g., according to size by gel electrophoresis, transferred and bound to a membrane filter such as a nitrocellulose or nylon membrane, and allowed to hybridize to a single labeled sequence (see, e.g., Nicoloso, M. et al., 1989, *Biochemical and Biophysical Research Communications* 159:1233–1241; Vernier, P. et al., 1996, *Analytical Biochemistry* 235:11–19). Other assays have been developed to study the hybridization kinetics of polynucleotides immobilized in agarose or polyacrylamide gels (see, e.g., Ikuta S. et al., 1987, *Nucleic Acids Research* 15:797–811; Kunitsyn, A. et al., 1996, *Journal of Biomolecular Structure and Dynamics* 14:239–244; Day, I. N. M. et al., 1995, *Nucleic Acids Research* 23:2404–2412), as well as hybridization to polynucleotide probes immobilized on glass plates (Beattie, W. G. et al., 1995, *Molecular Biotechnology* 4:213–225) including oligonucleotide microarrays (Stimpson, D. I. et al., 1995, *Proc. Natl. Acad. Sci. U.S.A.* 92:6379–6383).

In DNA microarray expression assays, a complex mixture of labeled, soluble sequences, derived, e.g., from expressed genes in a population of cells, is analyzed by hybridization to another complex set of sequences which are separated into individual species, each bound separately to a solid support. The amount of labeled sequence bound to each sequence on the support is used as a measure of the level of expression of that species in the cells (see, e.g., Schena et al., 1995, *Science* 270:467–470; Lockhart et al., 1996, *Nature Biotechnology* 14:1675–1680; Blanchard et al., 1996, *Nature Biotechnology* 14:1649; Ashby et al., U.S. Pat. No. 5,569,588;).

Equilibrium binding during hybridization of nucleic acids with complementary strands is related to (a) the similarity of the hybridizing sequences, (b) the concentration of the nucleic acid sequences, (c) the temperature, and (d) the salt concentration. Accordingly, it is well known that, depending on the temperature and salt conditions (i.e., the "stringency") of the hybridization or post-hybridization washing conditions, detection of bound labeled nucleic acid species can be limited to sequences which are nearly identical to the labeled sequence, or can be extended to include many related sequences. For example, "highly stringent" wash conditions may be employed so as to destabilize all mismatched heteroduplexes such that hybridization signals are obtained only from sequences that are perfectly homologous to the probe. Exemplary highly stringent conditions comprise, e.g., hybridization to filter-bound DNA in 5×SSC, 1% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., New York, N.Y., at p. 2.10.3). Alternatively, "moderate-" or "low-stringency" wash conditions may be used to identify sequences which are related, not just identical, to the probe, such as members of a multi-gene family, or homologous genes in a different organism. Such conditions are well known in the art (see, e.g., Sambrook et al., supra; Ausubel, F. M. et al., supra). Exemplary moderately stringent wash conditions comprise, e.g., washing in 0.2×SSC/0.1% SDS at 42° C. (Ausubel et al., 1989, supra). Exemplary low-stringency washing conditions include, e.g., washing in 0.2×SSC/0.1% SDS at room temperature (Ausubel et al., 1989, supra).

However, the exact wash conditions that are optimal for any given assay will depend on the exact nucleic acid sequence or sequences of interest, and, in general, must be empirically determined. There is no single hybridization or washing condition which is optimal for all nucleic acid preparations and sequences. Even the most optimized conditions can only partially distinguish between competing sequences, especially when the competing sequences are quite similar, or when some of the competing sequences are present in excess amounts, or at high total or local concentrations.

Consequently, in assays such as those utilizing DNA microarrays, wherein both the immobilized nucleic acid probes and the labeled nucleic acid samples are complex mixtures of sequences, it is difficult to differentiate between true hybridization by identical sequences and cross-hybridization by partially related sequences. For example, the high concentration of some common sequences increases their rate of hybridization, as well as the fraction of such sequences which are bound to any other sequence. The high local concentration of probe at the surface of a microarry may also trap mismatch binding partners. Further, the overwhelming variety of possible binding partners to a given probe sequence reduces both the rate and extent of true match binding by sequences of average or less than average abundance.

In such situations, it is usually impossible to obtain hybridization conditions which limit binding to true matches for all, or even the majority of sequences. As a result, it is not possible to determine the fraction of true match binding for any particular gene by hybridization alone, and, consequently, the measurement of moderately or poorly expressed nucleic acid sequences by hybridization assays such as DNA microarray analysis can be unreliable.

Discussion or citation of a reference herein shall not be construed as an admission that such reference is prior art to the present invention.

3. SUMMARY OF THE INVENTION

The present invention provides methods for determining the contribution of one or more particular polynucleotide species to a hybridization signal. In particular, the methods of the invention may be used to determine the "perfect match" or "true match" contribution to a hybridization signal. "Perfect match" and "true match", as used herein, refer to a polynucleotide sequence which is completely complementary to a particular probe. The terms "partial match", and "mismatch". as used herein, refer to polynucleotide sequences that hybridize to a particular probe with at least one non-complementary base pair. Such polynucleotide sequences are generally said to "cross-hybridize" to a probe.

The hybridization signals of the present invention comprise some measure of polynucleotide sequences in a sample which are hybridized to a given probe, or to a plurality of given probes. In general, such hybridization signals will include signals from perfect match polynucleotide sequences which hybridize to the probe or probes, as well as signals from one or more partial match or mismatch polynucleotide sequences which cross-hybridize to the probe or probes. Thus, the methods of the present invention may be used to determine the fractional contribution to a hybridization signal of perfect match polynucleotide sequences in a sample comprising one or more polynucleotide sequences which hybridize or cross-hybridize to a particular probe, i.e., the "perfect match contribution".

The invention applies concepts of nucleic acid equilibrium binding and kinetic washing so that one series of measurements can identify different polynucleotide species in a sample which hybridize to a probe. As a result, the invention permits a user to identify the fraction of a hybridization signal which is produced by a polynucleotide sequence that is truly complementary, i.e., the perfect-match, to the probe. Such a polynucleotide sequence will generally be the sequence of interest in a hybridization assay, e.g., to identify sequences derived from a particular gene or genes of interest which hybridize to one or more probes.

The principles of the method of the invention involve: (a) hybridizing polynucleotides to one or more polynucleotide probes of known sequences, (b) measuring over a time course of controlled dissociation the quantity of polynucleotide bound to each probe, thereby obtaining a "dissociation curve" for each probe, and (c) comparing or fitting the dissociation curve to a one or more "dissociation profiles".

Each dissociation profile is associated with the dissociation of a particular species of polynucleotide from the probe. As used herein, a polynucleotide species refers to a sequence or sequences of polynucleotide molecules which have a particular level or degree of complementarity to a given probe, or, alternatively to a sequence (or sequences) of polynucleotide molecules which have a particular range of levels or degrees of complementarity to a given probe. For example, one polynucleotide species may be the polynucleotides which are completely complementary to the probe, i.e., the perfect-match polynucleotide sequence. Other polynucleotide species may be those which cross-hybridize to the probe with one or more mismatches. Thus, the fractional contribution of perfect-match polynucleotide molecules to a hybridization signal is the fraction of the corresponding dissociation profile fit to the dissociation curve, i.e., the dissociation profile of the perfect-match polynucleotide sequence.

The dissociation curve is preferably obtained by sequentially washing the sample of bound polynucleotides under conditions which fractionally dissociate the hybridized polynucleotides to an extent related to their complementarity to the probe, and measuring the amount of labeled polynucleotide remaining.

In a preferred embodiment, the nucleic acid probes comprise oligonucleotides immobilized to a solid support or surface. For example, in one embodiment, the nucleic acid probe comprises an oligonucleotide bound to a membrane, such as a nylon or nitrocellulose membrane, of the type commonly used in DNA blotting assays. In a particularly preferred embodiment, a plurality of oligonucleotide probes are bound to a solid support, such as a glass surface, and comprise an array of distinct oligonucleotide sequences, each sequence having a specific, known location within the array. In an alternative embodiment, the probes comprise double-stranded polynucleotides corresponding to particular genes or gene fragments, and may be bound to a support or surface such as a glass surface or membrane.

In more detail, the present invention provides, in a first embodiment, a method for determining a contribution of one or more polynucleotide species to a hybridization signal of a plurality of polynucleotide species hybridized to molecules of a given probe. The method of the invention comprises comparing or fitting a "dissociation curve" to one or more "dissociation profiles", each dissociation profile being associated with a particular polynucleotide species suspected of hybridizing to one or more molecules of the given probe. The contribution of the one or more polynucleotide species to the hybridization signal is the contribution to the dissociation curve of the dissociation profiles associated with the one or more polynucleotide species.

The dissociation curve is preferably provided by a method comprising: (a) contacting a sample of polynucleotide molecules to molecules of the given probe under conditions which allow the polynucleotide molecules to hybridize to the molecules of the given probe; and (b) measuring the amount of polynucleotide molecules hybridized to the molecules of the given probe over a time period wherein a detectable fraction of bound polynucleotide molecules dissociates from the molecules of the given probe. In a specific embodiment the dissociation profile associated with a particular polynucleotide species is provided by a method comprising: (a) contacting a sample comprising the particular polynucleotide species to molecules of a test probe under conditions which allow the particular polynucleotide species to hybridize thereto; and (b) measuring the amount of particular polynucleotide species hybridized to the molecules of the test probe over a time period wherein a detectable fraction of the particular polynucleotide species dissociates from the molecules of the test probe. Alternatively, the dissociation profile associated with a particular polynucleotide species can be provided by a theoretical prediction of the form of the dissociation profile, wherein the shape parameters of the theoretical prediction are adjusted to match, e.g., known perfect match dissociation profiles under equivalent hybridization conditions.

In a preferred aspect of this first embodiment, the step of measuring the amount of polynucleotide molecules hybridized to molecules of the given probe comprises repeating the steps of (i) repeatedly washing the sample of polynucleotide molecules under conditions such that polynucleotide molecules fractionally dissociate from the molecules of the given probe and are removed therefrom, and (ii) measuring the amount of polynucleotide molecules which remain after each washing.

In another aspect of the first embodiment, the comparison or fit of the dissociation curve to the one or more dissociation profiles is the comparison or fit which minimizes an objective function of the difference between the dissociation curve and the one or more dissociation profiles. For example, in one particular aspect, the objective function is the absolute square of the difference of the dissociation curve and a combination of the one or more dissociation profiles. In an alternative aspect, the objective function is a x-squared function. In a particularly preferred embodiment, the one or more dissociation profiles consist of the dissociation profile associated with the perfect-match polynucleotide species.

The methods of the present invention are preferably performed by a computer system which analyzes input dissociation curves and dissociation profiles to determine the contribution of a perfect match polynucleotide species to a hybridization signal. Thus, in a second embodiment, the present invention provides a computer system for determining a contribution of one or more polynucleotide species to a hybridization signal of a plurality of polynucleotide species to molecules of a given probe. The computer system of the invention comprises a processor, and a memory coupled to the processor which encodes one or more programs. The programs cause the processor to perform a method comprising: (a) comparing or fitting a dissociation curve to one or more dissociation profiles, wherein each dissociation profile is associated with a particular polynucleotide species; (b) determining the value of an objective function of the difference between the dissociation curve and the one or more dissociation profiles; and (c) minimizing the determined value of the objective function, wherein the contribution of the one or more polynucleotide species to the hybridization signal is the contribution to the dissociation curve of the dissociation profiles associated with the one or more polynucleotide species. The dissociation curve and the dissociation profiles of this second embodiment are obtained or provided according to the same methods by which the dissociation curve and dissociation profiles of the first embodiment of this invention are provided.

Finally, in a third embodiment, the invention also provides computer readable media having a database recorded thereon in computer readable form which may be used in the methods and/or by the computer system of the invention. The database comprises one or more dissociation profiles wherein each dissociation profile is associated with a particular polynucleotide species hybridized to molecules of a probe. The dissociation profile associated with a particular polynucleotide species is obtained or provided by obtaining or providing the dissociation curve of each polynucleotide species, e.g., by a method comprising (a) contacting a sample comprising the particular polynucleotide species to molecules of a test probe under conditions which allow the particular polynucleotide species to hybridize or bind thereto, and (b) measuring the amount of the particular polynucleotide species hybridized or bound to the molecules of the probe over a time period wherein a detectable fraction of the particular polynucleotide species dissociates from the molecules of the test probe.

4. BRIEF DESCRIPTION OF THE DRAWINGS

Figure 5:
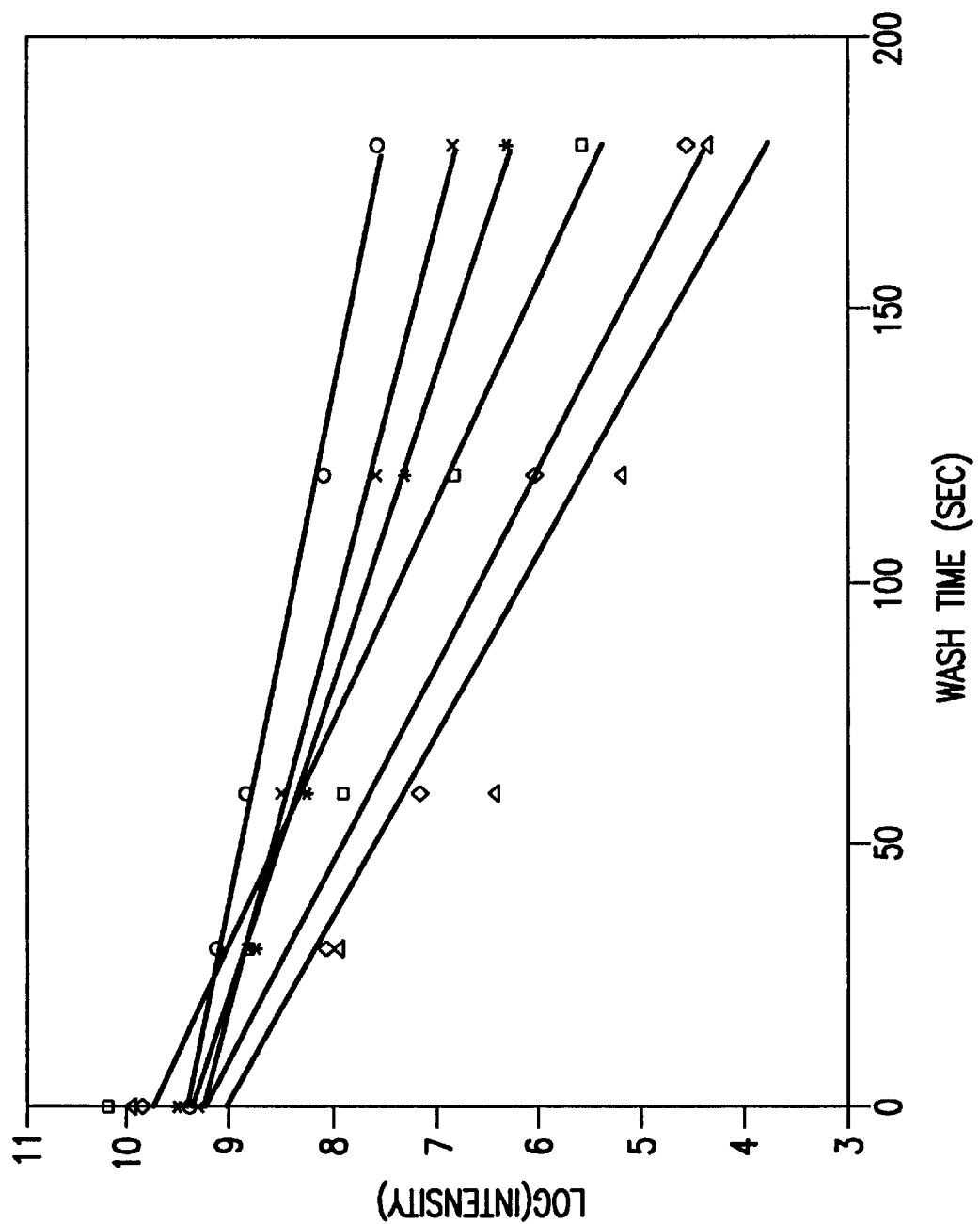

FIG. 5 is a plot of wash series data for the perfect match and five different mismatch duplexes listed in Table III: perfect match [Sequence A (○)], one mismatch [Sequence B (x)], three mismatches [Sequence C (*)], four mismatches [Sequence D (■)], five mismatches [Sequence G (♦)], and six mismatches [Sequence H (▲)]; the Log(Intensity) of each duplex is plotted vs. wash time, and is fit by an exponential decay model (straight lines).

Figure 4:
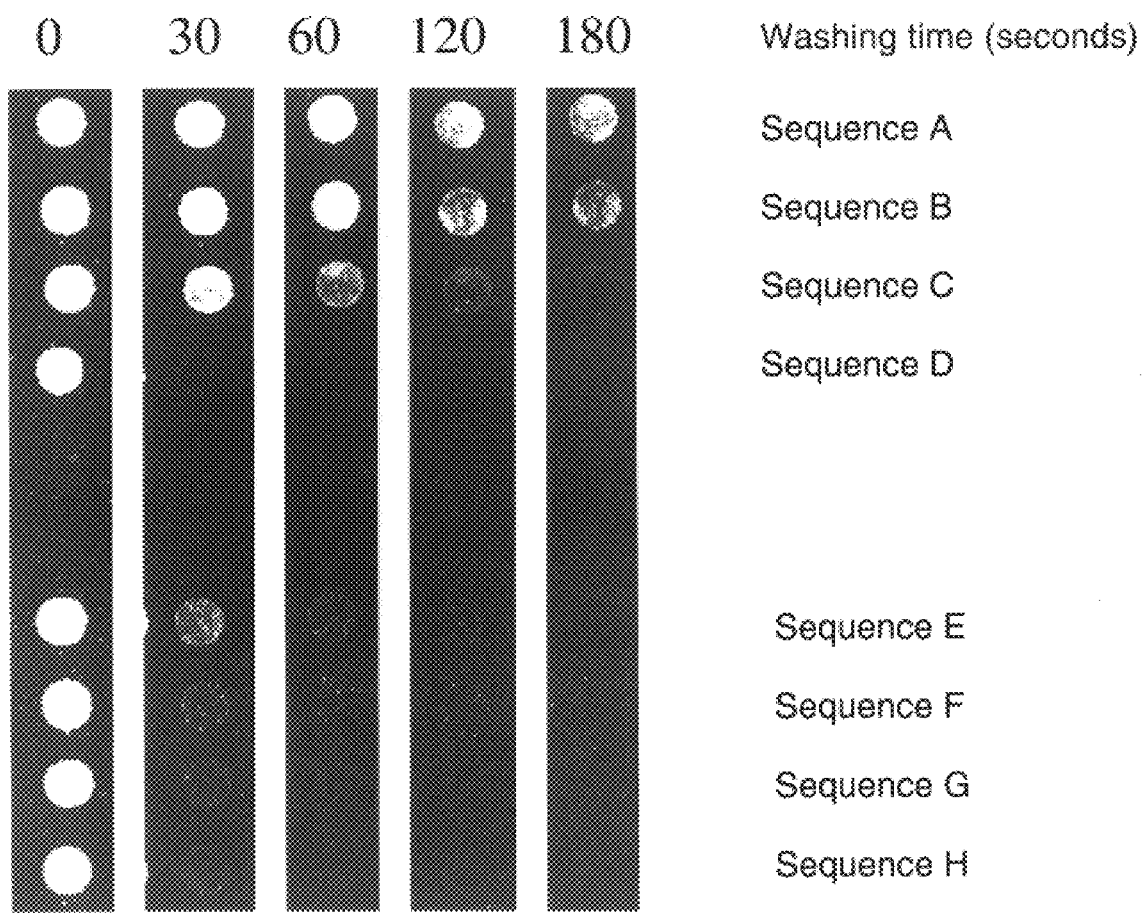
FIG. 4 shows fluorescent images of a glass slide spotted with DNA sequences A–H listed in Table III (SEQ ID NOS:4–11, respectively) after hybridization to a Cy3 labeled sequence complementary to Sequence A (SEQ ID NO:4) and washed for 30, 60, 120, and 180 second, respectively.
Figure 6:
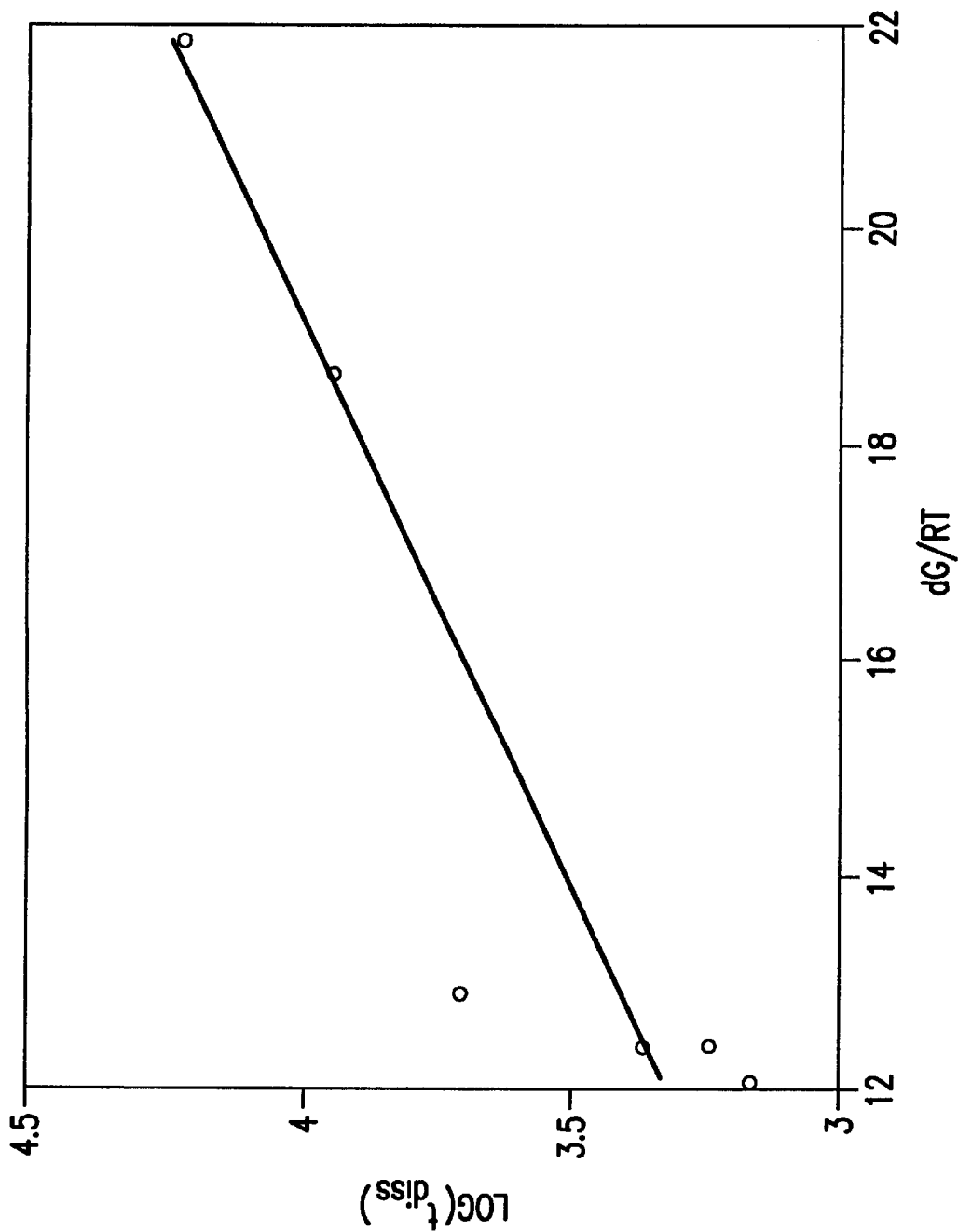

FIG. 6 is a logarithmic plot of the dissociation times derived from the exponential decay fits of the data in FIG. 4 vs. theoretical binding energies; the data is fit by linear regression to a straight line.

Figure 7:
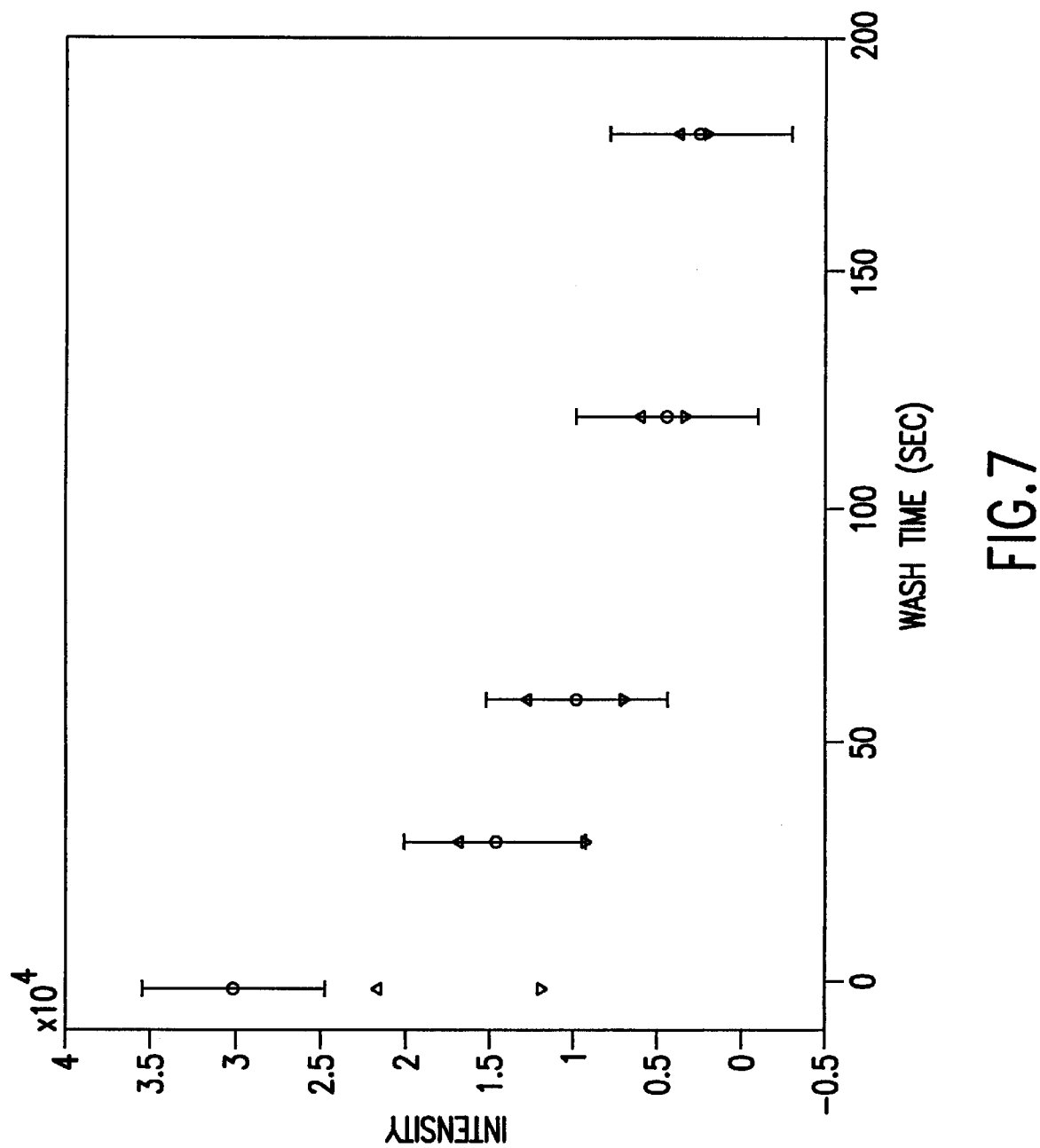

FIG. 7 is a plot of hypothetical dissociation curve data (○) which was calculated using the dissociation profiles plotted in FIG. 5; the actual contribution of the perfect match polynucleotide species (▼) to the dissociation curve is plotted along with the estimated contribution (▲) determined by minimizing a $\chi$-squared expression with no weighting factor (i.e., w=1).

Figure 8:
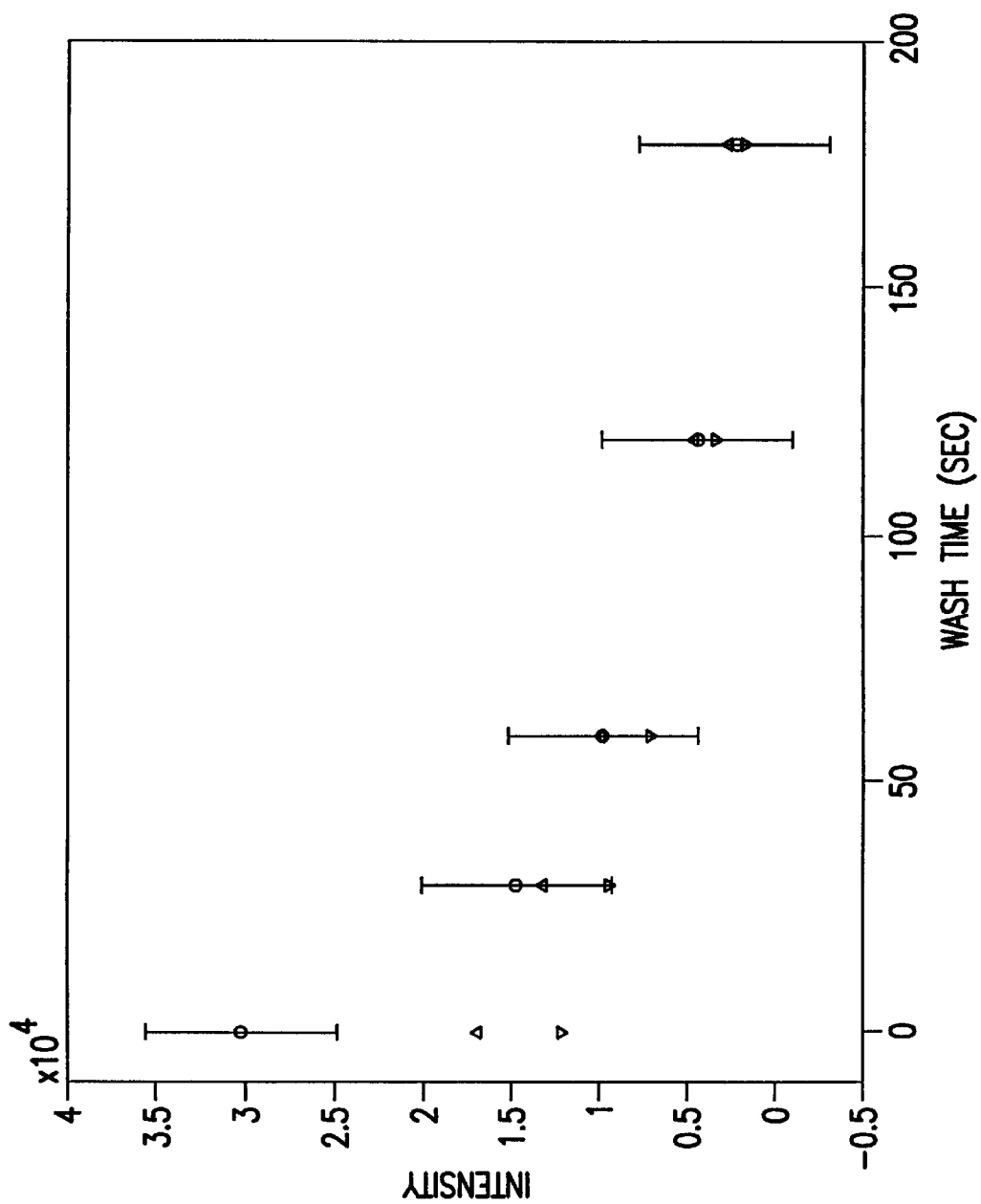

FIG. 8 is a plot of the hypothetical hybridization curve (○) and the actual perfect match contribution (▼) which are plotted in FIG. 6; the estimated perfect match contribution (▲) determined by a weighted $\chi$-squared expression (w=100) is also plotted.

5. DETAILED DESCRIPTION

The present invention includes methods of an assay for distinguishing cross-hybridization of polynucleotide molecules to one or more probe sequences. Specifically, the assay of this invention distinguishes the component of a hybridization signal which is produced by "perfect-match" polynucleotide sequences hybridizing to a probe sequence from the component or components produced by cross-hybridization of "partial-match" or "mismatch" polynucleotide sequences to the same probe sequence.

The polynucleotide molecules which may be analyzed by the methods of this invention include DNA molecules, such as, but by no means limited to genomic DNA molecules, cDNA molecules, and fragments thereof, such as oligonucleotides, STS's, etc. Polynucleotide molecules which may be analyzed by the methods of this invention also include RNA molecules, such as, but by no means limited to messenger RNA (mRNA) molecules, ribosomal RNA (rRNA) molecules, cRNA molecules (i.e., RNA molecules prepared from cDNA molecules that are transcribed in vitro) and fragments thereof.

Although for simplicity this disclosure often makes references to single probes (e.g., cDNA molecules are hybridized to "a probe" having a complementary sequence), it will be understood by those of skill in the art that often any particular hybridization signal of the invention will be obtained by hybridizing a polynucleotide sample to a plurality of probes (i.e., to a plurality of probe molecules) having identical sequences. In particular, the samples of polynucleotide molecules to be analyzed by the methods of the invention comprise complex mixtures of a plurality of sequences which hybridize or cross-hybridize to a probe or probes (i.e., to a probe sequence or to probe sequences) to various extents and with various kinetics. The extent to which any particular sequence initially hybridizes to a probe depends on several factors, including the level or degree of complementarity that sequence has to the sequence of the probe, the relative abundance of that sequence in the sample, the relative concentration and accessibility of the probe, and the extent to which hybridization has approached equilibrium. However, the kinetics of dissociation of the sequence from the probe depends only on the complementarity. In particular, each sequence will dissociate from a particular probe according a specific "dissociation profile" which can generally be characterized by a specific "dissociation-rate" or "off-rate". It is these dissociation profiles which are used to distinguish those sequences in a sample of polynucleotides which are completely complementary to the probe from those sequence with various levels of partial complementarity to the probe.

The invention is based at least in part on the discovery that the dissociation profiles of hybridized and cross-hybridized nucleic acid molecules are sufficiently distinct that individual dissociation profiles may be extracted, within the bounds of experimental error, from a dissociation curve generated by a plurality of polynucleotide sequences. Thus, the methods of the present invention allow one to identify nucleic acid molecules having various degrees of mismatch to a probe by identifying their individual components in a "dissociation curve", i.e., by identifying their "dissociation profiles".

The following subsections present the methods of the invention in greater detail. In particular, Section 5.1 first describes the general methods of the invention. Section 5.2 describes, in detail, systems for implementing the analytical methods of the invention. Finally, Section 5.3 describes, in detail, exemplary systems and probes for measuring hybridization and/or cross hybridization levels of polynucleotide molecules.

These descriptions are by way of exemplary illustrations, in increasing detail and specificity, of the general methods of the invention. These examples are non-limiting, and related variants that will be apparent to one of skill in the art are intended to be encompassed by the appended claims. Following these examples are descriptions of embodiments of the data gathering steps that accompany the general methods.

5.1. DETERMINING CROSS HYBRIDIZATION

Figure 1:
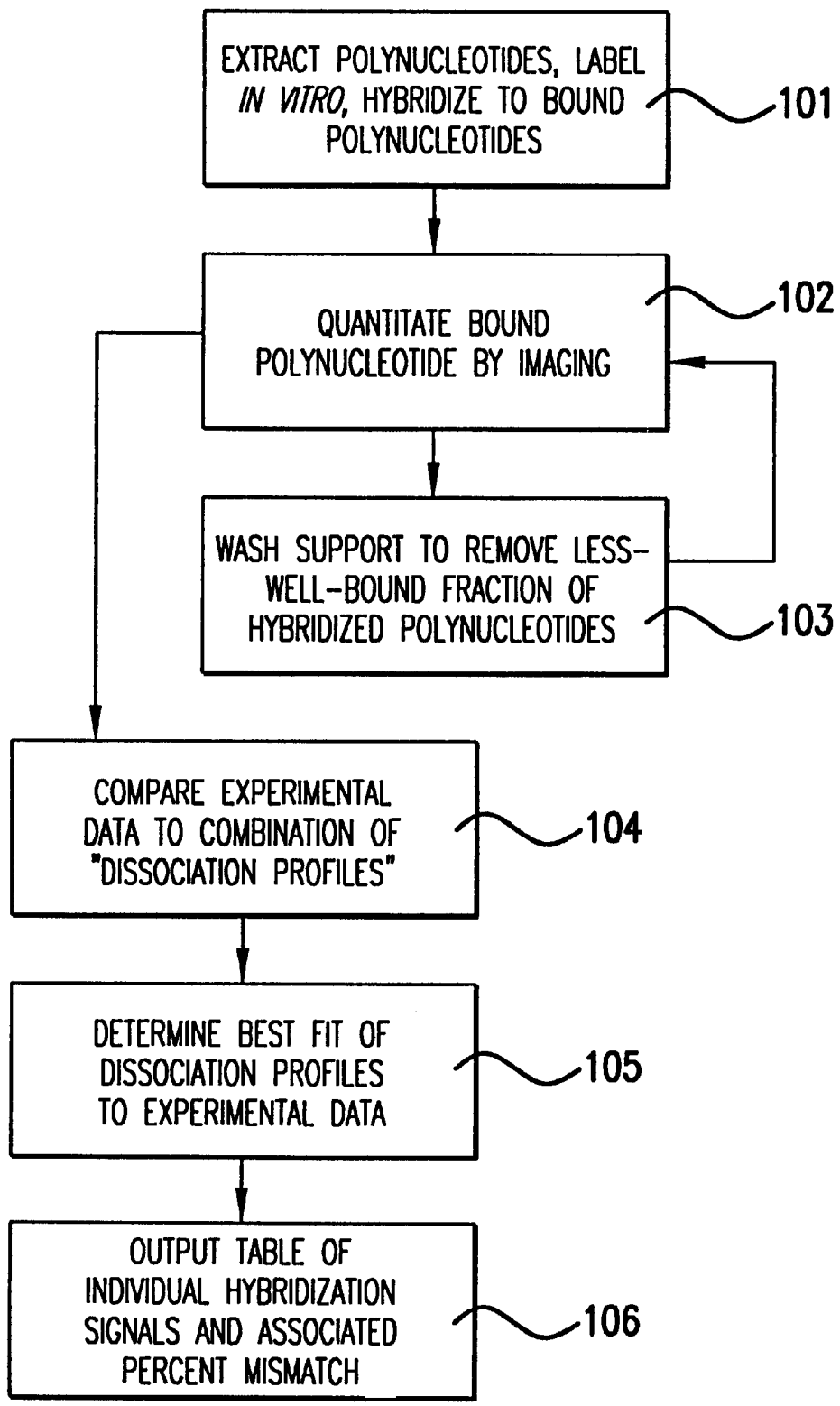
FIG. 1 illustrates generally the methods for determining cross hybridization according to this invention.

A flow chart illustrating the general method of the present invention is shown in FIG. 1. This embodiment determines a dissociation curve for a particular sample of polynucleotides hybridized to a particular probe or to a particular set of probes such as, e.g., an oligonucleotide microarray. Dissociation profile data is also obtained for hybridization of one or more polynucleotide species of known levels of complementarity to the same probe, to an identical probe, to an identical set of probes, or, more generally, to the particular type or "class" of probes. The dissociation curve is then compared to one or more dissociation profiles, and a best "fit" is determined. In particular, a level or fraction of each of the one or more dissociation profiles is determined which minimizes an objective function of the difference between the dissociation curve and the dissociation profiles. The contribution of a particular polynucleotide species to the total hybridization signal is then evaluated from its level in said fit. In one particular embodiment, the dissociation curve is compared or fit to the dissociation profile of the "perfect-match" polynucleotide species, i.e., the profile of the polynucleotide species which is completely complementary to the probe, so that its contribution to the hybridization signal can be determined.

In other embodiments of this invention, certain steps illustrated in FIG. 1 may be omitted or performed in orders other than as illustrated. For example, in certain embodiments the steps of obtaining dissociation profile data will already be derived, e.g., for a certain probe, or for a certain class of probes, and need not be performed separately for each analysis.

The following subsections describe, in detail, the methods of determining hybridization levels and obtaining dissociation curves (Section 5.1.1) and dissociation profiles (Section 5.1.2) therefrom. The analysis methods of the invention are described in Section 5.1.3.

5.1.1. DETERMINING HYBRIDIZATION LEVELS

In order to practice the methods of the present invention, dissociation curves are obtained or provided for a sample of polynucleotide molecules that is to be analyzed. The polynucleotide molecules to be analyzed by the methods of the present invention may be from any source. For example, the polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as, for example, cDNA molecules, or polynucleotide molecules synthesized by PCR, RNA molecules synthesized by in vitro transcription, etc. The sample of polynucleotide molecules can comprise, e.g., molecules of DNA, RNA, or copolymers of DNA and RNA.

In preferred embodiments, the polynucleotide molecules to be analyzed are prepared in vitro from nucleic acids extracted from cells. For example, in one embodiment, RNA is extracted from cells (e.g., total cellular RNA), and messenger RNA is purified from the total extracted RNA. cDNA is then synthesized from the purified mRNA using, e.g. oligo-dT or random primers. The polynucleotide molecules may be either fragmented or unfragmented. Preferably, the polynucleotide molecules are representative of the original nucleic acid population of the cell.

Preferably, the polynucleotide molecules to be analyzed by the methods of the invention are detectably labeled. The cDNA can be labeled directly, e.g., with nucleotide analogues, or a second, labeled cDNA strand can be made using the first strand as a template. Alternatively, the double-stranded cDNA can be transcribed into cRNA and labeled.

Preferably, the detectable label is a fluorescent label, e.g., by incorporation of nucleotide analogues. Other labels suitable for use in the present invention include, but are is not limited to, biotin, iminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}P$, $^{35}S$, $^{14}C$, and $^{125}I$. Fluorescent molecules suitable for the present invention include, but are not limited to, fluorescein and its derivatives, rhodamine and its derivatives, texas red, 5'carboxy-fluorescein ("FAM"), 2',7'-dimethoxy-4',5'-dichloro-6-carboxy-fluorescein ("JOE"), N,N,N',N'-tetramethyl-6-carboxy-rhodamine ("TTAMRA"), 6-carboxy-X-rhdoamine ("ROX"), HEX, TET, IRD40, and IRD41. Fluorescent molecules which are suitable for the invention further include: cyanine dyes, including but not limited to Cy3, Cy3.5, and Cy5; BODIPY dyes including but not limited to BODIPY-FL, BODIPY-TR, BODIPY-TMR, BODIPY-630/650, and BODIPY-650/670; ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the polynucleotide may be labeled by specifically complexing a first group to the polynucleotide. A second group, covalently linked to an indicator molecule, and which has an affinity for the first group could be used to indirectly detect the polynucleotide. In such an embodiment, compounds suitable for use as a first group include, but are not limited to, avidin and streptavidin. Compounds suitable for use as a second group include, but are not limited to, biotin and iminobiotin.

The labeled polynucleotide molecules to be analyzed by the methods of the invention are contacted to a probe, or to a plurality of probes under conditions that allow polynucleotide molecules having sequences complementary to the probe or probes to hybridize thereto (FIG. 1, step 101).

The probes of the invention comprise polynucleotide sequences which, in general, are at least partially complementary to at least some of the polynucleotide molecules to be analyzed. The polynucleotide sequences of the probe may be e.g., DNA sequences, RNA sequences, or sequences of a copolymer of DNA and RNA. For example, the polynucleotide sequences of the probe may be full or partial sequences of genomic DNA, cDNA, or mRNA sequences extracted from cells. The polynucleotide sequences of the probes may also be synthesized oligonucleotide sequences. The probe sequences can be synthesized either enzymatically in vivo, enzymatically in vitro, e.g., by PCR, or non-enzymatically in vitro.

The probe or probes used in the methods of the invention are preferably immobilized to a solid support or surface such that polynucleotide sequences which are not hybridized or bound to the probe or probes may be washed off and removed, without removing the probe or probes and any polynucleotide sequence bound or hybridized thereto. In one particular embodiment, the probes will comprise an array of distinct oligonucleotide sequences bound to a solid surface, such as a glass surface. Preferably, each particular oligonucleotide sequences is at a particular, known location on the surface. Alternatively, the probes may comprise double-stranded DNA comprising genes or gene fragments, or polynucleotide sequences derived therefrom, bound to a surface, e.g., a glass surface or a blotting membrane (e.g., a nylon or nitrocellulose membrane).

The conditions under which the polynucleotide molecules are contacted to the probe or probes preferably are selected for optimum stringency; i.e., under conditions of salt and temperature which create an environment close to the melting temperature for perfect match duplexes of the labeled polynucleotides and the probe or probes. For example, the temperature is preferably within 10–15° C. of the approximate melting temperature ("$T_m$") of a completely complementary duplex of two polynucleotide sequences (i.e., a duplex having no mismatches). Melting temperatures may be readily predicted for duplexes by methods and equations which are well known to those skilled in the art (see, e.g., Wetmur, 1991, *Critical Reviews in Biochemistry and Molecular Biology* 26:227–259), or, alternatively, such melting temperatures may be empirically determined using methods and techniques well known in the art, and described, e.g., in Sambrook, J. et al., eds., 1989, *Molecular Cloning: A Laboratory Manual,* 2nd Ed., Cold Spring Harbor Laboratory Press, Cold Spring Harbor, N.Y., at pp. 9.47–9.51 and 11.55–11.61; Ausubel et al., eds., 1989, *Current Protocols in Molecules Biology,* Vol. I, Green Publishing Associates, Inc., John Wiley & Sons, Inc., New York, at pp. 2.10.1–2.10.16. The exact conditions will depend on the specific polynucleotide molecules to be analyzed as well as on the particular probes, and may be determined by one of skill in the art (see, e.g., Sambrook et al., supra; Ausubel, F. M. et al., supra).

Hybridization times will most preferably be in excess of what is required for sampling of the bound polynucleotides (i.e., the probes or probes) by the labeled polynucleotides so that the mixture is close to equilibrium, and duplexes are at concentrations dependent on affinity and abundance rather than diffusion. However, the hybridization times are preferably short enough that irreversible binding interactions between the labeled polynucleotide and the probes and/or the surface do not occur, or are limited. For example, in embodiments wherein oligonucleotide arrays are used to probe a complex mixture of fragmented polynucleotides, typical hybridization times may be approximately 3–16 hours if no mixing of the hybridization solution is performed. Appropriate hybridization times for other embodiments will depend on the particular polynucleotide sequences and probes used, and may be determined by those skilled in the art (See, e.g., Sambrook, J. et al., supra).

After hybridization, generally the probe or probes are washed briefly, preferably in ice cold (i.e., approximately 0° C.) aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used (FIG. 1, 102).

For example, in embodiments wherein fluorescently labeled nucleotides or nucleotide analogues are used, signal detection is conveniently accomplished simply by detecting a fluorescent signal at the wavelength emitted by the fluorophore, e.g., fluorescent imaging of labeled nucleotides hybridized or cross-hybridized to a probe array using a fluorescent scanner. In other embodiments, wherein the nucleotide or nucleotide analogues are labeled by means of radioactive isotopes, e.g., $^{32}$P or $^{35}$S, hybridization may be detected by using autoradiography to detect the radioactive nucleotides. In yet other embodiments which use chemical labels such as biotin, the labeled polynucleotides may be detected, e.g., by means of a fluorescent probe or dye such as stepavidin.

The intensity of the measured signal from the label is an indicator of how many polynucleotide molecules have initially hybridized or bound to each probe, i.e., the hybridization "intensity" or hybridization "level". In general, the hybridization level of a particular probe includes both hybridization from perfect-match polynucleotide sequences, i.e., from polynucleotide sequences which hybridize to the probe with no mismatches, as well as cross-hybridization from partial-match or mismatch polynucleotide sequences, i.e., polynucleotide sequences having one or more mismatches to the probe.

After step 102 of measuring the initial hybridization level, the probe or probes are again washed (FIG. 1, step 103), preferably in warm, low-salt solution (i.e., under conditions of low to moderate stringency) for some time interval (referred to herein as the "wash interval", $\tau$) so that the individual polynucleotide species fractionally dissociate from the probe at rates that are dependent upon their level or degree of complementarity to the probe. Exemplary wash conditions comprise 0.01 to 1 M salt concentration at a temperature of approximately 40° C. below the predicted melting temperature of a completely complementary duplex. The wash interval will generally be on the order of 1 second (e.g., $\tau \approx 1$ s), but may, alternatively, be as long as several minutes. The optimal wash interval will depend on the specific polynucleotide sequences, the particular type of probe, and/or the extent to which equilibrium hybridization was achieved. Step 102 of imaging, described above, is then repeated, and the amount of detectable label is remeasured to determine the hybridization level after the wash interval, $\tau$.

Steps 102 and 103 of imaging and washing are repeated sequentially so that hybridization levels are measured over a plurality of wash intervals ($\tau_1, \tau_2, \ldots, \tau_N$), preferably until no detectable change is observed in the hybridization after subsequent washes. In a preferred embodiment, when no further change in the hybridization levels is observed after subsequent washes, the wash interval is approximately doubled (e.g., $\tau \approx 2$ s), and steps 102 and 103 are again sequentially repeated until there is no further loss of signal (i.e., no change in the hybridization levels is detected). In another preferred embodiment, the wash interval is then again increased, e.g., by a factor of approximately ten (e.g., $\tau \approx 10$ s), and steps 102 and 103 are again repeated until there is no further change detected in the hybridization levels. Preferably, at least four hybridization levels are measured over an equal number of wash intervals (i.e., $N \geq 4$). More preferably, hybridization levels are measured for ten or more wash intervals (i.e., $N \geq 10$). Still more preferably, hybridization levels are measured for 100 or more wash intervals ($N \geq 100$).

In an alternative embodiment of the above method, hybridization levels are monitored continuously throughout an extended wash interval, rather than periodically through sequential wash intervals.

In preferred embodiments, there is no irreversible binding of the polynucleotides to the probe or surface, and the final hybridization level is zero. However, in certain less preferred embodiments, irreversible binding does occur, and the final hybridization level is not zero (i.e., some detectable level of labeled polynucleotides remains bound to the probe even after extensive washing). In such embodiments, the final hybridization level is subtracted from each measured hybridization level.

The resulting series of measured hybridization levels comprises a measure of the dissociation of the different hybridized and cross-hybridized polynucleotide species from the probe as a function of time, $t_n$, after each wash interval; i.e., $t_n = \tau_1 + \tau_2 + \ldots + \tau_n$. Thus, the resulting series of measured hybridization levels obtained by the above described method comprises the "dissociation curve" for the polynucleotide sample.

5.1.2. OBTAINING DISSOCIATION PROFILES

Each polynucleotide species dissociates from a probe according to a particular function with respect to time after its initial hybridization thereto. This function is referred to herein as the "dissociation profile". In general, each dissociation profile is associated with a particular "dissociation-rate" or "off-rate", $k_{diss}$, which is a property of the polynucleotide species, and which characterizes the rate with which that species dissociates from the probe. Each dissociation profile is also characterized by a dissociation time, $t_{diss} = 1/k_{diss}$, which characterizes the time required for some specific fraction of the polynucleotide species to dissociate from the probe. As used herein, a "polynucleotide species" refers to a sequence or sequences of polynucleotide molecules which have a particular level or degree of complementarity to a given probe, or to sequences of polynucleotide molecules which have a particular range of levels of degrees of complementarity to a given probe. For example, one polynucleotide species will typically be those polynucleotide molecules which are completely complementary to a given probe and hybridize thereto with no mismatches, i.e., the perfect-match polynucleotide species. Other polynucleotide species will be polynucleotide molecules which hybridize to the probe with one or more mismatches.

According to the present invention, a dissociation profile is also obtained or provided for one or more polynucleotide species which is known or suspected of hybridizing or cross-hybridizing to the particular probe or probes. In a preferred embodiment, a dissociation profile is obtained for only one particular polynucleotide species, most preferably the perfect-match polynucleotide species to the probe. Preferably, the polynucleotide species for which dissociation profiles are obtained hybridize to the probe or probes at a level greater than 1% of the total species hybriding to the probe, more preferably at a level greater than 10% of the total species hybridizing to the probe, still more preferably at a level greater than 20% of the total species hybridizing to the probe.

The dissociation profiles of the invention may be provided according to any of several different methods. Preferably, a dissociation profile is obtained or provided for a particular polynucleotide species by determining the dissociation curve, according to the methods described in Section 5.1.1 above, for that polynucleotide species alone. In one embodiment, the dissociation profile of a particular polynucleotide species is obtained or provided in a separate hybridization assay with the same probe by determining the dissociation curve, according to the methods of Section 5.1.1. above, for a polynucleotide sample consisting of only that particular polynucleotide species. More preferably, the dissociation profiles of two or more polynucleotide species are obtained or provided simultaneously by measuring dissociation curves of a sample comprising the two or more polynucleotide species, wherein each polynucleotide species is labeled with a different detectable label so that the individual polynucleotide species may be detected simultaneously. For example, in one aspect of this embodiment, the polynucleotide species are each labeled with different fluorescent dyes which fluoresce at different wavelengths. Thus, dissociation curves can be measured for each polynucleotide species, according to the methods of Section 5.1.1 above, by measuring fluorescence intensities for each wavelength. Because the dissociation of different polynucleotide species is measured simultaneously, this alternative embodiment is more stable to experimental error, and is therefore preferred.

In one embodiment, the one or more dissociation profiles are obtained or provided concurrently with the dissociation curve of the polynucleotide sample of interest (i.e., the sample for which the cross-hybridization contribution(s) to the hybridization signal are to be determined). Specifically, the dissociation profile is obtained from the same probe (e.g., the same spot on a microarray) using a second, differentially labeled, simultaneous hybridization sample (e.g., using two-color fluorescence hybridization protocols) which contains the polynucleotide species for which dissociation profiles are to be determined (e.g., the perfect-match species such as the target gene of interest or the complementary oligonucleotide sequence to an oligonucleotide probe).

In an alternative embodiment, the dissociation profiles of the invention are obtained or provided from the dissociation curves of individual polynucleotide species hybridizing or cross-hybridizing to a different, second probe, such as at a different oligonucleotide spot on an oligonucleotide array. In such an embodiment, the second probe is chosen to have a binding energy for the perfect match duplex which is similar or identical to the binding energy for the perfect match duplex of the first probe. Such binding energies may be readily predicted by those skilled in the art using numerical models which are well known in the art, including the nearest neighbor model (SantLucia, J., 1988, *Proc. Natl. Acad. Sci. U.S.A.* 95:1460–1465), or by using computer implementations of such models, such as HybSimulator (Hyndman, D. et al., 1996, *Biotechniques* 20:1090–1097).

Still less preferably, the dissociation profiles of the invention can be obtained or provided by theoretical prediction of the form of the dissociation profiles, with shape parameters adjusted to match the dissociation profiles of exemplary perfect-match dissociation profiles, preferably under identical hybridization conditions. Such exemplary perfect-match dissociation profiles may be obtained, e.g., from perfect-match polynucleotide species which hybridize to different sequences, such as to a different oligonucleotide spot on an oligonucleotide array. In general, polynucleotide species of different sequences will hybridize with different binding energies, and their dissociation profiles will therefore be characterized by different dissociation rates and dissociation times. Specifically, the dissociation time, $t_{diss}$, for a polynucleotide which hybridizes to a probe with a binding energy $\Delta G$ can be computed by Equation 1, below.

$$t_{diss} = \alpha \exp\left(\beta \frac{\Delta G}{RT}\right) \quad (1)$$

In Equation 1, above, R denotes the ideal gas constant. T is the temperature in degrees Kelvin. The binding energy $\Delta G$ may be determined by any theoretical method or model which provides a value related to the actual binding energy. Such models include the nearest neighbor model (SantLucia, J., 1988, *Proc. Natl. Acad. Sci. U.S.A.* 95:1460–1465), as well as computer implementations of such models, such as HybSimulator (Hyndman, D. et al., 1996, *Biotechniques* 20:1090–1097).

$\alpha$ and $\beta$ are fitting parameters which are fit to experimental data, e.g., from least squares fitting, for particular hybridization conditions. For example, it is expected that $\alpha$ and $\beta$ will have certain values for hybridization, e.g., to an oligonucleotide probe of a particular length in a microarray, and other, different values for hybridization under different conditions, e.g., to an oligonucleotide probe in bulk solution.

In particular, $\alpha$ and $\beta$ may be determined by fitting Equation 1 (e.g., by linear regression; see, for example, Press et al., 1996, *Numerical Recipes in C*, 2nd Ed., Cambridge Univ. Press. Chapter 14, Section 2) to dissociation data from "equivalent" hybridizing pairs (e.g., other perfect-match polynucleotide species hybridizing to other probes such as to other probes on a given hybridization array) with known or determined dissociation rates, $t_{diss}$, and binding energies $\Delta G$ which are known or may be calculated using well known theoretical models as discussed above.

Once appropriate values for $\alpha$ and $\beta$ have been determined, the dissociation time of a particular polynucleotide species hybridized to the particular probe of interest can be extrapolated from Equation 1 above using a value for the binding energy determined from a theoretical model as described above. A suitable dissociation profile can then be created, e.g., from a theoretical model, as discussed in Section 5.1.3 below, characterized by the determined dissociation time. In a particularly preferred embodiment, the dissociation profile is an exponential decay of the form $A(t)=\exp(-k_{diss} t)$, where the dissociation rate $k_{diss}=1/t_{diss}$.

5.1.3. COMPUTATIONAL METHODS

As explained supra, dissociation curves for a sample of labeled polynucleotides hybridizing to a particular probe are provided by incrementally measuring hybridization intensity levels of polynucleotides to the probe after each wash interval. In the following, the variable "R" refers generally to the measured signal from the detectably labeled polynucleotides which remain hybridized to a particular probe after washing, i.e., the hybridization level or intensity. In detail, $R_n$ represents the hybridization intensity after the n'th washing.

In general, the hybridization level is specified as a function of time, $t_n$, measured from the time of initial hybridization. The time of the n'th wash interval is referred to as $\tau_n$. Thus, the time $t_n$ is the summation of wash intervals up to and including $\tau_n$.

$$t_n = \tau_1 + \tau_2 + \tau_3 + \ldots + \tau_n \quad (2)$$

Alternatively, if washing is monitored continuously, $t_n$ is simply the elapsed wash time. Therefore, $R(t_n)$ is the hybridization intensity after time $t_n$ from the initial hybridization measurement, i.e., after the n'th wash. Preferably, $R(t_n)$ is normalized with respect to the initial hybridization intensity, so that $R(0)=1$.

Each polynucleotide species which initially hybridizes to a particular probe will dissociate from the probe with a particular "dissociation profile", D, which reflects the amount of that polynucleotide species that remains bound to the probe at some time, t, after hybridization. Dissociation profiles are provided for each polynucleotide species, as described in Section 5.1.2 above, e.g., by measuring dissociation curves for each individual polynucleotide species which hybridizes or cross-hybridizes to the probe. Thus, dissociation profiles $D_i(t_m')$ may be provided for each polynucleotide species i as a function of time $t_m'$ of the m'th wash after hybridization. As with the dissociation curves R, the dissociation profiles are preferably normalized with respect to the initial hybridization level, i.e., so that $D_i(0)=1$.

In general, the actual wash times $\{\tau_n\}$ used to obtain the dissociation curve will be different from the wash times $\{\tau_m'\}$ used to obtain each dissociation profile. Thus, in general, $t_n$ and $t_m'$ are not equal. In such instances, it is necessary to provide for interpolating of the dissociation profiles to obtain dissociation profile values at the needed time values. This interpolation method is preferably accomplished either by spline fitting or, more preferably, by model fitting.

In spline fitting, the dissociation profile data are interpolated by summing products of an appropriate spline interpolation function, S, multiplied by the measured data values, as illustrated by the following equation.

$$D_i(t) = \sum_m S(t - t_m) D_i(t_m) \quad (3)$$

The variable "t" refers to an arbitrary value of the time after initial hybridization at which dissociation profile data are to be evaluated. In general, S may be any smooth, or at least piece-wise continuous, function of limited support having a width characteristic of the structure expected in the dissociation profile function. An exemplary width can be chosen to be the distance over which the response function being interpolated falls from 90% to 10% of its asymptotic value. Exemplary S functions include linear and Gaussian interpolation.

More preferably, the dissociation profile data are interpolated by approximating each profile by a single parameterized function, most preferably by a function corresponding to a particular theoretical model. In a particularly preferred embodiment, the normalized dissociation profile of the i'th polynucleotide species, $D_i$, is represented as an exponential decay.

$$A_i(t) = e^{-k_i t} \quad (4)$$

The dissociation rate, $k_i$, is selected independently for each polynucleotide species. For example, in one preferred embodiment, the off-rate is selected so that for each measured time, $t_m'$, the sum of the squares of the difference between the measured normalized dissociation profile and the exponential decay function for each measured time interval is minimized.

$$\min_{\{c_i\}} \sum_m \{(D_i(t_m') - A_i(t_m'))^2\} \quad (5)$$

This preferable parameter adjustment method is well known in the art as a least squares fit of $D_i(\,)$ to $A_i(\,)$ (see, e.g., Press et al., 1996, *Numerical Recipes in C*, 2nd Ed., Cambridge Univ. Press, Chapters 10, 14). Other possible, less preferable, model functions are based on polynomial fitting, for example by various known classes of polynomials.

The hybridization intensity at the different wash times $\{t_n\}$ is compared with one or more dissociation profiles for particular polynucleotide species hybridizing or cross-hybridizing to the probe. In a particularly preferred embodiment, the dissociation curve is compared with the dissociation profile corresponding to the perfect-match polynucleotide species, so that the fraction of the hybridization signal which is due to hybridization of perfect-match polynucleotide sequences (e.g., the target sequence) to the probe is determined.

In one preferred embodiment, the dissociation curve is compared to a weighted sum of two or more individual, normalized dissociation profiles.

$$\sum_i N_i D_i \quad (6)$$

Here, $N_i$ is the fraction of the polynucleotide species i which contributes to the total hybridization signal. Preferably, one of the dissociation profiles is the true-match dissociation profile.

Preferably, the best-fit over all possible values of $N_i$ is determined from the minimization of the related least squares approximation problem.

$$\min_{\{N_i\}} \sum_n \left\{ \left( R(t_n) - \sum_i N_i D_i(t_n) \right)^2 \right\} \quad (7)$$

In Equation 7, the absolute square of the difference of the hybridization level and the summation of dissociation profiles is summed for each time, $t_n$, for which the hybridization level has been measured. The best-fit of the hybridization level in terms of the dissociation profile is determined from the minimization of this sum with respect to the amount of each polynucleotide species initially hybridizing the probe, $N_i$. Minimization of least squares Equations 6 and 7 is performed using any of the many available numerical methods (see, e.g., Press et al., 1996, *Numerical Recipes in C*, 2nd Ed., Cambridge Univ. Press. Chapters. 10, 14; Branch et al., 1996, *Matlab Optimization Toolbox User's Guide*, Mathworks (Natick, Mass.).

More preferably, the dissociation curve is compared to a single dissociation profile, most preferably the dissociation profile of the true-match polynucleotide species. In such an embodiment, the dissociation profile is preferably fit to the dissociation curve, e.g., by minimizing a $\chi$-squared quantity defined as $$\min_{\{\alpha\}} \chi^2(\alpha) = \chi_1^2 + \chi_2^2 \quad (8)$$

where

-continued $$\chi_1^2 = \sum_n \frac{(\alpha D(t_n) - R(t_n))^2}{\sigma_{R(t_n)}^2} \quad (9)$$

$$\chi_2^2 = \left[\sum_{n \subset E} \frac{(\alpha D(t_n) - R(t_n))}{\sigma_{R(t_n)}^2}\right]^2 \bigg/ \left[\sum_{n \subset E} \sigma_{R(t_n)}^{-2}\right] \quad (10)$$

In Equation 10 above, E denotes the set of points $\alpha D(t_n) > R(t_n)$. Accordingly, E will depend on the value of $\alpha$. $\sigma^2_{R(m)}$ is the expected variance (e.g., the standard deviation) of the data points $R(t_n)$ of the dissociation curve.

Minimization of Equation 8 works best when wash data collection extends out to times where very little or none of the other components (e.g., the cross hybridizing components) of the dissociation curve remain. The resulting estimate, i.e., $\alpha D(t_n)$, tends to approach the dissociation curve, $R(t_n)$, at large wash times while tending to fall below the dissociation curve at early wash times, with the difference being attributed to cross-hybridization of other polynucleotide species.

In general, however, the above embodiment is biased in that it tends to overestimate the fraction of the dissociation profile (e.g., the perfect match fraction), thereby undercorrecting for the cross hybridization of other polynucleotide species. This bias can be reduced, in an alternative embodiment, by increasing the magnitude (i.e., the weight) of the penalty term, $\chi^2_2$, in Equation 8, according to Equation 11, below.

$$\min_{\{\alpha\}} \chi^2(\alpha) = \chi_1^2 + w\chi_2^2 \quad (11)$$

where w can be any number greater than or equal to unity. This embodiment is particularly preferred in instances wherein the latest wash times still have measurable hybridization signal, and significant mismatch contribution remains.

In a preferred aspect of this alternative embodiment, w is chosen by solving Equation 12 below.

$$w = \frac{\sum_{n > n_1} R^2(t_n)}{\sum_{n > n_1} \sigma_{R(t_n)}^2} \quad (12)$$

Preferably, $n_1$ is chosen in Equation 12 so that the wash times $t_{n > n1}$ are those of about the later one-third of the wash times.

5.2. IMPLEMENTATION SYSTEMS AND METHODS

Figure 3:
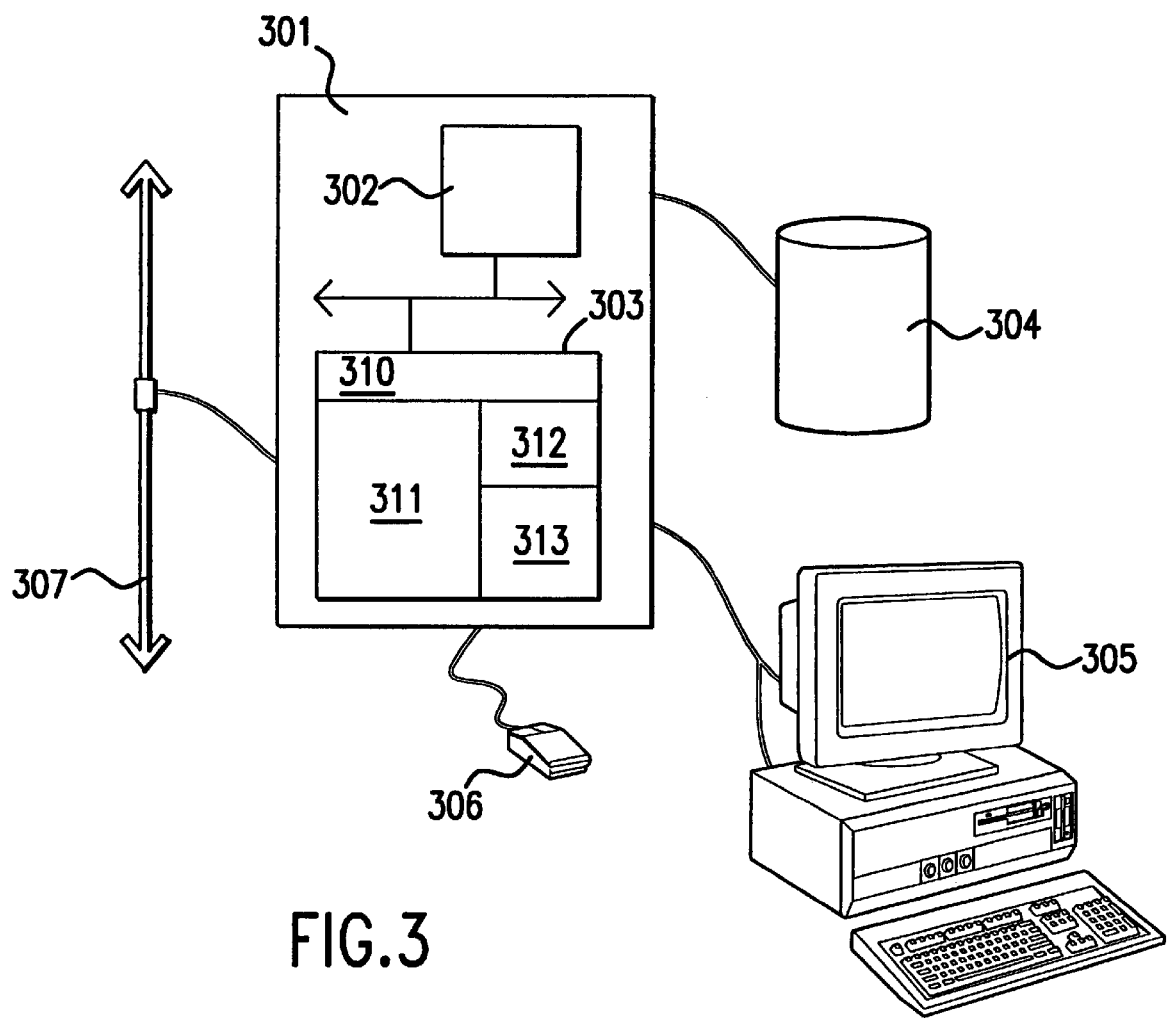
FIG. 3 illustrates an exemplary computer system for implementing of the analytic methods of the invention.

The analytic methods described in the previous subsections can preferably be implemented by use of the following computer systems, and according to the following methods. FIG. 3 illustrates an exemplary computer system suitable for implementation of the analytic methods of this invention. Computer system 301 is illustrated as comprising internal components and being linked to external components. The internal components of this computer system include processor element 302 interconnected with main memory 303. For example, computer system 301 can be an Intel Pentium-based processor of 200 MHz or greater clock rate and with 32 MB or more of main memory.

The external components include mass storage 304. This mass storage can be one or more hard disks which are typically packaged together with the processor and memory. Such hard disks are typically of 1 GB or greater storage capacity. Other external components include user interface device 305, which can be a monitor and a keyboard, together with pointing device 306, which can be a "mouse", or other graphical input devices (not illustrated). Typically, computer system 301 is also linked to a network link 307, which can be part of an Ethernet link to other local computer systems, remote computer systems, or wide area communication networks, such as the Internet. This network link allows computer system 301 to share data and processing tasks with other computer systems.

Loaded into memory during operation of this system are several software components, which are both standard in the art and special to the instant invention. These software components collectively cause the computer system to function according to the methods of the invention. The software components are typically stored on mass storage 304. Software component 310 represents an operating system, which is responsible for managing computer system 301 and its network interconnections. This operating system can be, for example, of the Microsoft Windows™ family, such as Windows 95, Windows 98, or Windows NT, or, alternatively, a Macintosh operating system, or a Unix operating system. Software component 311 represents common languages and functions conveniently present in the system to assist programs implementing the methods specific to this invention. Languages that can be used to program the analytic methods of the invention include, for example, C, C++, and, less preferably, JAVA. Most preferably, the methods of this invention are programmed in mathematical software packages which allow symbolic entry of equations and high-level specification of processing, including algorithms to be used, thereby freeing a user of the need to procedurally program individual equations and algorithms. Such packages include, e.g., Matlab from Mathworks (Natick, Mass.), Mathematica from Wolfram Research (Champaign, Ill.), or S-Plus from Math Soft (Seattle, Wash.). Accordingly, software component 312 represents the analytic methods of this invention as programmed in a procedural language or symbolic package.

In a preferred embodiment, the computer contains a software component 313 which may be additional software for determining (i.e., calculating) the dissociation profile for a specific polynucleotide species hybridizing to a particular probe. Such a dissociation profile will then be calculated according to the methods described in Section 5.1.2 above. Alternatively, software component 313 may also be a database of dissociation profiles of polynucleotide species. Such a database may comprise, for example, the dissociation rates and/or dissociation times corresponding to a plurality of polynucleotide species hybridizing to a particular probe, or, more preferably, a plurality of probes.

In an exemplary implementation, to practice the methods of the present invention, hybridization level data (i.e., a dissociation curve) is first loaded in the computer system 301. These data can be directly entered by the user from monitor and keyboard 305, or from other computer systems linked by network connection 307, or on removable storage media such as a CD-ROM or floppy disk (not illustrated). Next the user causes execution of analysis software 312 which performs the steps of determining and minimizing the value of an objective function of the difference between the dissociation curve and one or more dissociation profiles. The dissociation profiles may be directly entered by the user, or, alternatively, may be calculated by or extracted from the database of software component 313.

The present invention also provides databases of dissociation profiles for use in determining the fractions of polynucleotide molecules in a sample having particular levels of complementarity to a probe. The databases of this invention include dissociation profiles for a plurality of polynucleotide species corresponding to a plurality of levels of complementarity to a particular probe, or, more generally, to a particular class of probes (e.g., for oligonucleotide microarrays). More preferably, the database includes dissociation profiles for several probes, or, still more preferably, for several classes of probes. Preferably, such a database will be in a computer readable form and recorded on a computer readable medium that can be loaded into a computer system 301. Exemplary computer readable media include, but are not limited to, removable storage media such as a CD-ROM or floppy disk (not illustrated), mass storage media (304), the main memory (303) of a computer system used to implement the methods of the invention, and the main memory of one or more other computers including other computers linked by network connection (307).

Alternative systems and methods for implementing the analytic methods of this invention are intended to be comprehended within the accompanying claims. In particular, the accompanying claims are intended to include the alternative program structures for implementing the methods of this invention that will be readily apparent to one of skill in the art.

5.3. MEASUREMENT OF HYBRIDIZATION LEVELS

In general, the hybridization methods of the present invention can be performed using any probe or probes which comprise a polynucleotide sequence and which are immobilized to a solid support or surface. For example, as describe supra, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probe may be full or partial sequences of genomic DNA, cDNA, or mRNA sequences extracted from cells. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support or surface which may be either porous or non-porous. For example, the probes of the invention may be polynucleotide sequences which are attached to a nitrocellulose or nylon membrane or filter. Such hybridization probes are well known in the art (see, e.g., Sambrook et al., Eds., 1989, *Molecular Cloning: A Laboratory Manual,* 2nd ed., Vol. 1–3, Cold Spring Harbor Laboratory, Cold Spring Harbor, N.Y.). Alternatively, the solid support or surface may be a glass or plastic surface.

5.3.1. MICROARRAYS GENERALLY

In a particularly preferred embodiment, hybridization levels are measured to microarrays of probes consisting of a solid phase on the surface of which are immobilized a population of polynucleotides, such as a population of DNA or DNA mimics, or, alternatively, a population of RNA. Specifically, a microarray is an array of less the 6.25 $cm^2$ in size. Microarrays can be employed, e.g., for analyzing the transcriptional state of a cell, such as the transcriptional states of cells exposed to graded levels of a drug of interest, or to graded perturbations to a biological pathway of interest.

In preferred embodiments, a microarray comprises a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably the microarrays are small, usually smaller than 5 $cm^2$, and they are made from materials that are stable under binding (e.g., nucleic acid hybridization) conditions. Preferably, a given binding site or unique set of binding sites in the microarray will specifically bind (e.g., hybridize) to the product of a single gene in a cell (e.g., to a specific mRNA, or to a specific cDNA derived therefrom). However, as discussed supra, in general other, related or similar sequences will cross hybridize to a given binding site. Although there may be more than one physical binding site per specific RNA or DNA, for the sake of clarity the discussion below will assume that there is a single, completely complementary binding site.

The microarrays of the present invention include one or more test probes, each of which has a polynucleotide sequence that is complementary to a subsequence of RNA or DNA to be detected. Each probe preferably has a different nucleic acid sequence. The position of each probe on the solid surface is preferably known. In one embodiment, the microarray is a high density array, preferably having a density greater than about 60 different probes per 1 $cm^2$. In one embodiment, the microarray is an array (i.e., a matrix) in which each position represents a discrete binding site for a product encoded by a gene (i.e., an mRNA or a cDNA derived therefrom), and in which binding sites are present for products of most or almost all of the genes in the organism's genome. For example, the binding site can be a DNA or DNA analogue to which a particular RNA can specifically hybridize. The DNA or DNA analogue can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often to at about 75%, more often to at least about 85%, even more often to about 90%, and still more often to at least about 99%. Alternatively, however, "picoarrays" may also be used. Such arrays are microarrays which contain binding sites for products of only a limited number of genes in the target organism's genome. Generally, a picoarray contains binding sites corresponding to fewer than about 50% of the genes in the genome of an organism.

Preferably, the microarray has binding sites for genes relevant to the action of a drug of interest or in a biological pathway of interest. A "gene" is identified as an open reading frame (ORF) which encodes a sequence of preferably at least 50, 75, or 99 amino acids from which a messenger RNA is transcribed in the organism or in some cell in a multicellular organism. The number of genes in a genome can be estimated from the number of mRNAs expressed by the organism, or by extrapolation from a well characterized portion of the genome. When the genome of the organism of interest has been sequenced, the number of ORF's can be determined and mRNA coding regions identified by analysis of the DNA sequence. For example, the genome of *Saccharomyces cerevisiae* has been completely sequenced, and is reported to have approximately 6275 ORFs longer than 99 amino acids. Analysis of these ORFs indicates that there are 5885 ORFs that are likely to encode protein products (Goffeau et al., 1996, *Science* 274:546–567). In contrast, the human genome is estimated to contain approximately $10^5$ genes.

5.3.2. PREPARING PROBES FOR MICROARRAYS

As noted above, the "probe" to which a particular polynucleotide molecules specifically hybridizes according to the invention is a complementary polynucleotide sequence. In one embodiment, the probes of the microarray are DNA or DNA "mimics" (e.g., derivatives and analogues) corresponding to at least a portion of each gene in an organism's genome. In another embodiment, the probes of the microarray are complementary RNA or RNA mimics.

DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtained, e.g., by polymerase chain reaction (PCR) amplification of gene segments from genomic DNA, cDNA (e.g., by RT-PCR), or cloned sequences. PCR primers are preferably chosen based on known sequence of the genes or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between about 20 bases and about 50,000 bases, and usually between about 100 bases and about 2,000 bases in length, and still more usually between about 300 bases and about 1000 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399–5407; McBride et al., 1983, *Tetrahedron Lett.* 24:246–248). Synthetic sequences are typically between about 15 and about 500 bases in length, more typically between about 20 and about 50 bases. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566–568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207–209).

5.3.3. ATTACHING PROBES TO THE SOLID SURFACE

The probes are attached to a solid support or surface, which may be made, e.g., from glass, plastic (e.g., polypropylene, nylon), polyacrylamide, nitrocellulose, or other materials. A preferred method for attaching the nucleic acids to a surface is by printing on glass plates, as is described generally by Schena et al, 1995, *Science* 270:467–470. This method is especially useful for preparing microarrays of cDNA (See also, DeRisi et al, 1996, *Nature Genetics* 14:457–460; Shalon et al., 1996, *Genome Res.* 6:639–645; and Schena et al., 1995, *Proc. Natl. Acad. Sci. U.S.A.* 93:10539–11286). Blanchard discloses the use of an ink jet printer for oligonucleotide synthesis (U.S. application Ser. No. 09/008,120, filed Jan. 16, 1998).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767–773; Pease et al., 1994, *Proc. Natl. Acad. Sci. U.S.A.* 91:5022–5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687–690). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids. Res.* 20:1679–1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

5.3.4. TARGET POLYNUCLEOTIDE MOLECULES

As described, supra, the polynucleotide molecules which may be analyzed by the present invention may be from any source, including naturally occurring nucleic acid molecules, as well as synthetic nucleic acid molecules. In a preferred embodiment, the polynucleotide molecules analyzed by the invention comprise RNA, including, but by no means limited to, total cellular RNA, poly(A)$^+$ messenger RNA (mRNA), fraction thereof, or RNA transcribed from cDNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). In an alternative embodiment, which is preferred for S. cerevisiae, RNA is extracted from cells using phenol and chloroform, as described in Ausubel et al. (Ausubel et al., eds., 1989, *Current Protocols in Molecular Biology*, Vol III, Green Publishing Associates, Inc., John Wiley & Sons, Inc., New York, at pp. 13.12.1–13.12.5). Poly(A)+ RNA is selected by selection with oligo-dT cellulose. Cells of interest include, but are by no means limited to, wild-type cells, drug-exposed wild-type cells, modified cells, diseased cells and, in particular, cancer cells.

In one embodiment, RNA can be fragmented by methods known in the art, e.g., by incubation with $ZnCl_2$, to generate fragments of RNA. In one embodiment, isolated mRNA can be converted to antisense RNA synthesized by in vitro transcription of double-stranded cDNA in the presence of labeled dNTPs (Lockhart et al., 1996, Nature Biotechnology 14:1675).

In other embodiments, the polynucleotide molecules to be analyzed may be DNA molecules such as fragmented genomic DNA, first strand cDNA which is reverse transcribed from mRNA, or PCR products of amplified mRNA or cDNA.

5.3.5. HYBRIDIZATION TO MICROARRAYS

As described supra, nucleic acid hybridization and wash conditions are chosen so that the polynucleotide molecules to be analyzed by the invention (referred to herein as the "target polynucleotide molecules") "specifically bind" or "specifically hybridize" to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, Current Protocols in Molecular Biology, Greene Publishing and Wiley-Interscience, New York. When the cDNA microarrays of Schena et al. are used, typical hybridization conditions are hybridization in 5×SSC plus 0.2% SDS at 65 ° C. for four hours, followed by washes at 25° C. in low stringency wash buffer (1×SSC plus 0.2% SDS), followed by 10 minutes at 25° C. in higher stringency wash buffer (0.1× SSC plus 0.2% SDS) (Shena et al., 1996, Proc. Natl. Acad. Sci. U.S.A. 93:10614). Useful hybridization conditions are also provided in, e.g., Tijessen, 1993, Hybridization With Nucleic Acid Probes, Elsevier Science Publishers B.V. and Kricka, 1992, Nonisotopic DNA Probe Techniques, Academic Press, San Diego, Calif.

6. EXAMPLES

The following examples are presented by way of illustration of the previously described invention, and are not limiting of that description.

6.1. MEASUREMENT OF DISSOCIATION CURVES

In this example, dissociation curves were recorded for labeled polynucleotide sequences hybridized to an oligonucleotide array. Dissociation profiles corresponding to various degrees of mismatch to the probes were also obtained and evaluated to determine the corresponding dissociation-rates.

Oligonucleotide arrays were synthesized with 169 sequences according to the methods described in Section 5.3 above. The array sequences included 164 20-mer sequences which were derived from "barcode" sequences used in the yeast deletion consortium 96-pack chr5_3. These sequences ranged from 0 to 100% (i.e., from insignificant to complete) match to the designed sequence D11, specified in Table I below.

The arrays were simultaneously hybridized with the complement to D11 labeled with Cy3 at the 5'-end, and with a double-mismatch complement to D11 labeled with Cy5 at the 5'-end. Specifically, the double mismatch oligonucleotide contained the nucleic acid substitutions at positions 7 and 14 of D11 indicated in the second row of Table I.

TABLE I

| Polynucleotide: | Sequence: | Sequence: |
| --- | --- | --- |
| D11 | 5'-CCGCGATACCAATTCATAGA-3' | SEQ ID NO:1 |
| D11 complement | 5'-TCTATGAATTGGTATCGCGG-3' | SEQ ID NO:2 |
| D11 double mismatch | 5'-TCTATGGATTGGTGTCGCGG-3' | SEQ ID NO:3 |

The hybridizations were carried out using 100 $\mu$L solutions of 6×SSC buffer with 0.005% Triton-X-100 containing 0.5 to 5 nM of both labeled oligonucleotides for 15 to 60 minutes at either 22 or 60° C. The different hybridization times had no effect on the ensuing wash kinetics. However, the hybridization temperature had a significant effect. Specifically, hybridization at 22° C. led to higher levels of nonspecific binding at all spots on the array, minimizing the differences in wash kinetics. Thus, all subsequent experiments were performed using the 60° C. hybridization temperature.

After hybridization, the arrays were washed in ice cold 6×SSC/0.01% Triton-X-100 for 3 seconds, followed by washing for 3 seconds in ice cold 6×SSC, and then dried and scanned with a dual-laser confocal scanner which simultaneously imaged the Cy3 and Cy5 dyes on the array. The hybridization levels determined from this first scan were taken to be the initial hybridization levels of the polynucleotides [i.e., as R(0)].

The arrays were subsequently washed in one to four second wash intervals in either 6×SSC or 0.6×SSC at 30° C., dried, and rescanned. The arrays washed in 6×SSC were also washed for 1 to 3 seconds in ice cold 0.6×SSC to remove salt before drying and scanning.

Figure 2:
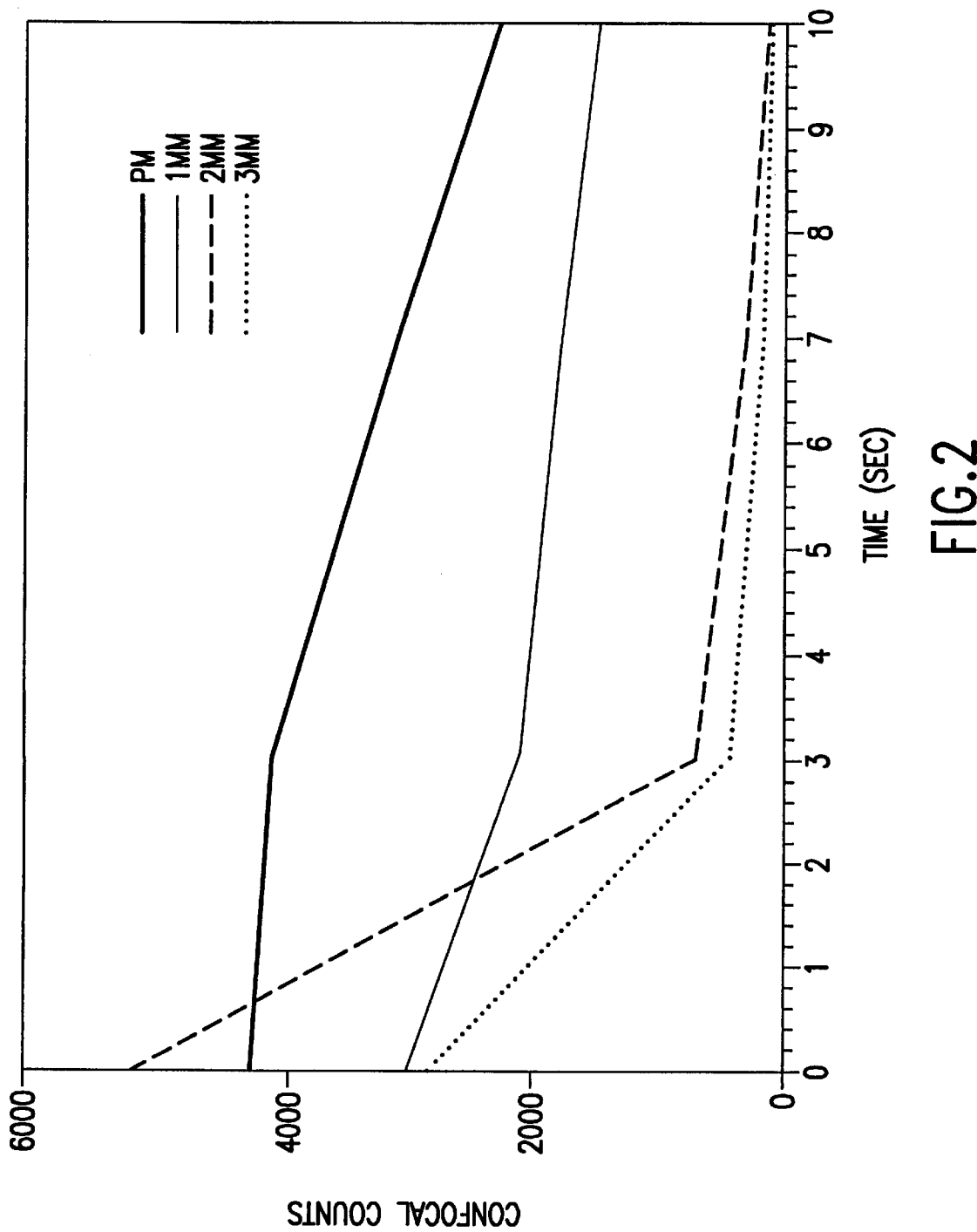
FIG. 2 illustrates exemplary dissociation profiles.

Spots on each of the thus acquired images were quantitated by averaging pixel intensities for each fluorescent label across each spot after background subtraction. Intensities from serial images are plotted in FIG. 2 for individual signals corresponding to hybridization of an oligonucleotide to a probe with perfect match, i.e., no base mismatches (PM); hybridization of an oligonucleotide to a probe with one base mismatch (1MM); hybridization of an oligonucleotide to a probe with two base mismatches (2MM); and hybridization of an oligonucleotide to a probe with three base mismatches (3MM). These dissociation profiles were analyzed according to Equation 4 in Section 5.1.3 above to determine the corresponding dissociation-rates ("off-rates"), which are listed below in Table II.

TABLE II

| Polynucleotide Species: | Off-Rate (sec⁻¹): |
| --- | --- |
| PM | 0.067 |
| 1MM | 0.072 |
| 2MM | 0.547 |
| 3MM | 0.593 |

6.2. DETERMINATION OF DISSOCIATION PROFILES

This example illustrates how dissociation profiles may be determined by a different method than the one illustrated in Section 6.1 above. In particular, the example demonstrates the calculation of dissociation profiles according to a theoretical model using empirically determined parameters for the particular hybridization conditions.

Wash series data were obtained for a perfect match and seven different mismatch duplexes of 20 base oligonucleotides. The nucleotide sequences of these eight oligonucleotides are provided in Table III below. In more detail, eight different 20mer oligonucleotides, containing from zero to six mismatches with respect to a reference 20mer (i.e., the "perfect match" oligonucleotide), were spotted onto a glass slide according to the following procedure: The oligonucleotides were synthesized with primary amino groups on their 3'-ends. A solution containing 5×SSC and 25 µM of the different oligonucleotides was spotted onto silylated (free aldehyde) microscope slides (CEL Associates, Houston, Tex.). After drying for 12 hours, the slides were washed twice in a 0.2% SDS solution and twice in water (one minute for each wash) to remove the excess salt and unbound DNA. The slides were then incubated in a 90 mM sodium borohydride solution to reduce the free aldehydes. The slides were then rinsed three times in a 0.2% SDS solution and twice in water (one minute for each wash).

TABLE III

| Probe Sequence | 5'-GAGACAGCTCTTCCGAACAT-3' | SEQ ID NO:4 |
| --- | --- | --- |
| Sequence A (perfect match) | 5'-ATGTTCGGAAGAGCTGTCTC-3' | SEQ ID NO:5 |
| Sequence B (1 mismatch) | 5'-ATGTTCGGGAGAGCTGTCTC-3' | SEQ ID NO:6 |
| Sequence C (3 mismatches) | 5'-ATGTTCGGAGAGGCTGTCTC-3' | SEQ ID NO:7 |
| Sequence D (4 mismatches) | 5'-ATGTTGGGAAGAGGTGTGTG-3' | SEQ ID NO:8 |
| Sequence E (4 mismatches) | 5'-TTGTTCGGTTGTGCTGTCTC-3' | SEQ ID NO:9 |
| Sequence F (4 mismatches) | 5'-TTGTTCGGTCGTGCTGTCTC-3' | SEQ ID NO:10 |
| Sequence G (5 mismatches) | 5'-TTGTTCGGCCATGCTGTCTC-3' | SEQ ID NO:11 |
| Sequence H (6 mismatches) | 5'-AAGAACGGAAGAGCAGACAC-3' | SEQ ID NO:12 |

A Cy3 labeled 20mer, complementary to the reference 20mer, was hybridized to one of the spotted slides for 20 minutes at 50° C. The 50 µl hybridization mixture contained 6× SSPE-T (0.9 M NaCl, 70 mM phosphate buffer pH 7.4, 7 mM EDTA, and 0.005% triton-x 100) and 5 nM of the Cy3 labeled 20mer. Following the hybridization, the glass slide was briefly rinsed with 4° C. 0.06× SSPE-T to remove the unbound oligonucleotides and salt. The slide was then scanned using a General Scanning ScanArray 3000 confocal scanner. To determine the off-rates for the different oligonucleotides, the slide was placed in a beaker containing 500 ml of 0.6× SSPE-T at 50° C. The slide was removed from the beaker, after wash times of 30, 60, 120, and 180 seconds, briefly rinsed with cold 0.06 SSPE-T, scanned, and returned to the beaker. The resulting images are shown in FIG. 4. The hybridization signals from these images were quantitated, and the data was used to determine the off-rates.

FIG. 5 is a plot of the Log(Intensity) of the measured hybridization signal for each polynucleotide species vs. the wash time. In particular, FIG. 5 shows the Log(Intensity) of the measured hybridization signal for Sequences A, B, C, D, G and H in Table III. The data were fit by an exponential decay model, indicated by the straight lines in FIG. 5, and dissociation times, $t_{diss}$, were extracted from the fit of each polynucleotide species. The binding energy ΔG of each polynucleotide species to the probe at 50° C. was also calculated according to the nearest neighbor model using HybSimulator (Hyndman et al., 1996, *Biotechniques* 20:1090–1097).

FIG. 6 shows a plot of the thus determined log($t_{diss}$) vs. ΔG/RT (T=50° C.). The values were fit to a straight line by standard techniques of linear regression, and the slope, m, and intercept, b, were used to determine β and α, respectfully, from Equation 1. The thus determined values are provided in Table IV, below.

TABLE IV

| α (seconds) | β |
| --- | --- |
| 9.2 | 0.092 |

6.3. FITTING A DISSOCIATION CURVE TO A PERFECT MATCH DISSOCIATION PROFILE

In this example, an exemplary dissociation curve is compared (i.e., fit) to the dissociation profile corresponding to the perfect-match polynucleotide species, i.e., the polynucleotide species hybridizing to the probe with no mismatches. The example demonstrates that the contribution of the perfect match polynucleotide to the total hybridization signal can be effectively determined according to the methods of this invention.

FIG. 7 illustrates a theoretical dissociation curve (circles with error bars) calculated from the dissociation profiles of FIG. 5 which are described in Section 6.2 above. Specifically, this theoretical dissociation curve was synthesized as an arithmetic sum of the individual dissociation profiles wherein the perfect match dissociation profile has a multiplicative factor of unity, and each of the five mismatch dissociation profiles had a multiplicative factor of 0.2. The perfect match profile is indicated in FIG. 7 by the lower set of triangle symbols. The calculated dissociation curve was fit to the perfect match dissociation profile by minimizing the $\chi^2$ (α) expression of Equation 8 in Section 5.1.3 above.

The estimate thus obtained for the perfect match contribution to the dissociation curve is indicated in FIG. 7 by the upper set of triangle symbols. This estimate is biased high, as expected, and is about midway between the compound data (i.e., the dissociation curve) and the actual perfect match contribution. Thus, only about one-half of the cross-hybridization is corrected in the total hybridization signal.

The calculated dissociation curve was again fit to the perfect match dissociation profile, this time by minimizing the $\chi^2$ (α) expression of Equation 11, using w=100. The result is shown in FIG. 8. Again, the theoretical dissociation curve data is indicated by the circles with error bars. The actual contribution of the perfect match dissociation profile is indicated by the lower set of triangle symbols, while the contribution estimated by minimizing Equation 11 is indicated by the upper set of triangle symbols. The estimated contribution is now much closer to the actual contribution, and the cross hybridization is >¾ corrected.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for determining a contribution of a reference polynucleotide to hybridization of polynucleotides in a sample to a test probe that is immobilized on a first solid surface, said method comprising comparing a dissociation curve for said hybridization to a dissociation profile for the reference polynucleotide, wherein:
   (a) the dissociation curve is provided by a method comprising
      (i) contacting a sample to the test probe under conditions that allow polynucleotides in the sample to hybridize to the test probe,
      (ii) repeatedly washing the test probe under conditions such that some fraction of the hybridized polynucleotides dissociates from the test probe, and
      (iii) measuring hybridization of the polynucleotides in the sample to the test probe after each of a plurality of said washing steps, over a time period wherein a detectable fraction of hybridized polynucleotides dissociates from the test probe; and
   (b) the dissociation profile is provided by a method comprising
      (i) contacting the reference polynucleotide to a reference probe that is immobilized on a second solid surface under conditions that allow the reference polynucleotide to hybridize to the reference probe,
      (ii) repeatedly washing the reference probe under conditions such that some fraction of the hybridized polynucleotides dissociates from the reference probe, and
      (iii) measuring hybridization of the reference polynucleotide to the reference probe after each of a plurality of said washing steps, over a time period wherein a detectable fraction of the polynucleotide dissociates from the reference probe; and
wherein the contribution of the reference polynucleotide to hybridization to the test probe is the contribution of the dissociation profile to the dissociation curve.

2. The method of claim 1, wherein the reference probe is identical to the test probe.

3. The method of claim 1, wherein the test probe and the reference probe are the same probe.

4. The method of claim 3, wherein the step of contacting a sample to the test probe is performed concurrently with the step of contacting the reference polynucleotide to the reference probe.

5. The method of claim 3 wherein the step of contacting a sample to the test probe is performed at a different time than the step of contacting the reference polynucleotide to the reference probe.

6. The method of claim 1 wherein said comparing comprises minimizing the value of an objective function of the difference between the dissociation curve and the dissociation profile.

7. The method of claim 6 wherein the objective function is an absolute square of the difference of the dissociation curve and the dissociation profile.

8. The method of claim 6 wherein the objective function is a $\chi$-squared quantity.

9. The method of claim 1, wherein the reference polynucleotide is detectably labeled.

10. The method of claim 9, wherein the detectable label is a fluorescent label.

11. The method of claim 10, wherein the fluorescent label is fluorescein, rhodamine, texas red, or a derivative thereof.

12. The method of claim 10, wherein the fluorescent label is FAM, JOE, ROX, HEX, TET, IRD40, IRD41, a cyanine dye, a BODIPY dye, or an ALEXA dye.

13. The method of claim 12, wherein the cyanine dye is selected from the group consisting of Cy3, Cy3.5, and Cy5.

14. The method of claim 12, wherein the BODIPY dye is selected from the group consisting of BODIPY-FL, BODIPY-TR, BODIPY-TMR, BODIPY-630/650, and BODIPY-650/670.

15. The method of claim 12, wherein the ALEXA dye is selected from the group consisting of ALEXA-488, ALEXA-532, ALEXA-546, ALEXA-568, and ALEXA-594.

16. The method of claim 9, wherein the detectable label is a radioactive isotope.

17. The method of claim 16, wherein the radioactive isotope is selected from the group consisting of $^{32}P$, $^{35}S$, $^{14}C$, and $^{125}I$.

18. The method of claim 9, wherein the detectable label is an electron rich molecule.

19. The method of claim 18, wherein the electron rich molecule is selected from the group consisting of ferritin, hemocyanin, and colloidal gold.

20. The method of claim 9, wherein the detectable label comprises a first chemical group specifically complexed to the reference polynucleotide,
   wherein said first chemical group is detected by contacting the first chemical group with a second chemical group; and
   wherein said second chemical group:
      (i) has binding affinity for the first chemical group, and
      (ii) is covalently linked to an indicator molecule.

21. The method of claim 9, wherein the detectable label is biotin or imminobiotin.

22. The method of claim 1, wherein the reference polynucleotide is a naturally occurring nucleic acid.

23. The method of claim 22, wherein the naturally occurring nucleic acid molecules are genomic DNA isolated from cells or an organism.

24. The method of claim 22, wherein the naturally occurring nucleic acid is RNA isolated from cells or an organism.

25. The method of claim 1, wherein the reference polynucleotide is RNA expressed by a cell or organism, cDNA derived therefrom, or cRNA derived from said cDNA.

26. The method of claim 25, wherein the RNA is messenger RNA.

27. The method of claim 1, wherein the reference polynucleotide is a synthetic nucleic acid.

28. The method of claim 1, wherein the polynucleotide is cDNA.

29. The method of claim 1, wherein the reference polynucleotide is a polynucleotide synthesized by polymerase chain reaction.

30. The method of claim 1, wherein the test probe comprises a DNA sequence.

31. The method of claim 30, wherein the DNA sequence of the test probe comprises a genomic DNA sequence.

32. The method of claim 30, wherein the DNA sequence of the test probe comprise a cDNA sequence.

33. The method of claim 1, wherein the test probe comprises an RNA sequence.

34. The method of claim 33, wherein the RNA sequence of the test probe comprises a messenger RNA sequence.

35. The method of claim 1, wherein the test probe comprises a sequence of DNA analogues.

36. The method of claim 1, wherein the test probe comprises a sequence of RNA analogues.

37. The method of claim 1, wherein the first solid surface and the second solid surface are each a cellulose filter.

38. The method of claim 1, wherein the first solid surface and the second solid surface are each a nylon membrane.

39. The method of claim 1, wherein the first solid surface and the second solid surface are each a glass surface.

40. The method of claim 1, wherein the first solid surface and the second solid surface are each a nonporous surface.

41. The method of claim 1, wherein the first solid surface and the second solid surface are each a porous surface.

42. The method of claim 1, wherein the test probe is part of an array of probes.

43. The method of claim 42, wherein the array of probes is a microarray.

44. The method of claim 43, wherein the probes of the microarray are complementary to fewer than 50% of the genes in the genome of an organism.

45. The method of claim 43, wherein the probes of the microarray are complementary to at least 50% of the genes in the genome of an organism.

46. The method of claim 45, wherein the probes of the microarray are complementary to at least 75% of the genes in the genome of an organism.

47. The method of claim 45, wherein the probes of the microarray are complementary to at least 85% of the genes in the genome of an organism.

48. The method of claim 45, wherein the probes of the microarray are complementary to at least 90% of the genes in the genome of an organism.

49. The method of claim 45, wherein the probes of the microarray are complementary to at least 99% of the genes in the genome of an organism.

50. The method of claim 43, wherein each probe of the microarray comprises a polynucleotide sequence of between 20 bases and 50,000 bases.

51. The method of claim 50, wherein each probe of the microarray comprises a polynucleotide sequence of between 100 bases and 2,000 bases.

52. The method of claim 51, wherein each probe of the microarray comprises a polynucleotide sequence of between 300 1 bases and 1,000 bases.

53. The method of claim 43, wherein the density of the probes of the microarray is greater than 60 different probes per $cm^2$.

54. The method of claim 43, wherein the probes of the microarray comprise single stranded oligonucleotides of 10 to 50 bases.

55. The method of claim 43, wherein the probes of the microarray comprise single stranded oligonucleotides of greater than 50 bases.

56. The method of claim 43, wherein the probes of the microarray comprise single stranded polynucleotides of greater than 100 bases.

57. The method of claim 43, wherein the probes of the microarray comprise Sequence-Tagged Sites.

58. The method of claim 1, wherein the step of contacting the reference polynucleotide to the reference probe is carried out by a method comprising contacting a reference sample to the reference probe,
said reference sample comprising molecules of a plurality of different polynucleotides,
said plurality of different polynucleotides comprising the reference polynucleotide, and
each of said different polynucleotides being differentially labeled.

59. The method of claim 3, wherein:
polynucleotides in the sample contacted to the test probe are labeled with a first label, and
the reference polynucleotide contacted to the reference probe is labeled with a second label, said second label being distinguishable from the first label.

60. A method for determining a contribution of a reference polynucleotide to hybridization of polynucleotides in a sample to a test probe that is immobilized on a solid surface, said method comprising comparing a dissociation curve for said hybridization to a dissociation profile for the reference polynucleotide, in which:
the dissociation curve is provided by a method comprising
(a) contacting a sample to the test probe under conditions that allow polynucleotides in the sample to hybridize to the test probe;
(b) repeatedly washing the test probe under conditions such that some fraction of the hybridized polynucleotides dissociates from the test probe; and
(c) measuring hybridization of the polynucleotides in the sample to the test probe after each of a plurality of said washing steps, over a time period wherein a detectable fraction of hybridized polynucleotides dissociates from the test probe;
wherein the dissociation profile is provided from a theoretical prediction of a dissociation time, $t_{diss}$, of the reference polynucleotide from a reference probe provided by:

$$t_{diss} = \alpha \exp\left(\beta \frac{\Delta G}{RT}\right)$$

wherein R is the ideal gas constant, T is the temperature in degrees Kelvin, $\Delta G$ is the binding energy, and $\alpha$ and $\beta$ are fitting parameters that are fit to experimental data; and
wherein the contribution of the polynucleotide to molecules hybridized to the test probe is the contribution of the dissociation profile to the dissociation curve.

61. The method of claim 60, wherein the dissociation profile is an exponential decay function.

62. The method of claim 1 or 60, wherein the reference polynucleotide hybridizes to the test probe with no base mismatches.

63. A method for determining the contribution of each of a plurality of polynucleotides to hybridization of polynucleotides in a sample to a test probe that is immobilized on a first solid surface, said method comprising comparing a dissociation curve for said hybridization to a dissociation profile for each of the plurality of polynucleotides, in which:
  (a) the dissociation curve is provided by a method comprising
    (i) contacting a sample to the test probe under conditions that allow polynucleotides in the sample to hybridize to the test probe;
    (ii) repeatedly washing the test probe under conditions such that some fraction of the hybridized polynucleotides dissociates from the test probe; and
    (iii) measuring hybridization of polynucleotides in the sample to the test probe after each of a plurality of said washing steps, over a time period wherein a detectable fraction of hybridized polynucleotides dissociates from the test probe, and
  (b) the dissociation profile for each of the plurality of polynucleotides is provided by a method comprising
    (i) contacting each of the plurality of polynucleotides to a reference probe that is immobilized on a second solid surface under conditions that allow each of the plurality of polynucleotides to hybridize to the reference probe;
    (ii) repeatedly washing the reference probe under conditions such that some fraction of the hybridized polynucleotides dissociates from the reference probe; and
    (iii) measuring hybridization of each of the plurality of polynucleotides to the reference probe after each of a plurality of said washing steps, over a time period wherein a detectable fraction of each of the plurality of polynucleotides dissociates from the reference probe,
wherein the contribution of each of the different polynucleotide molecules to hybridization to the test probe is the contribution of the dissociation profile for each of the plurality of polynucleotides to the dissociation curve.

64. The method of claim 63, wherein each of the plurality of polynucleotides has a different polynucleotide sequence.

65. The method of claim 63, wherein each of the plurality of polynucleotides is contacted separately to the reference probe.

66. The method of claim 63, wherein each of the plurality of polynucleotides is differentially labeled.

67. The method of claim 66, wherein each of the plurality of polynucleotides is contacted concurrently to the reference probe.

68. A method for determining the contribution of each of a plurality of polynucleotides to hybridization of polynucleotides in a sample to a test probe that is immobilized on a solid surface, said method comprising comparing a dissociation curve for said hybridization to a dissociation profile for each of the plurality of polynucleotides, in which:
  (a) the dissociation curve is provided by a method comprising
    (i) contacting a sample to the test probe under conditions that allow polynucleotides in the sample to hybridize to the test probe;
    (ii) repeatedly washing the test probe under conditions such that some fraction of the hybridized polynucleotides dissociates from the test probe; and
    (iii) measuring hybridization of the polynucleotides in the sample to the test probe after each of a plurality of said washing steps, over a time period wherein a detectable fraction of hybridized polynucleotides dissociates from the test probe, and
  (b) the dissociation profile for each of the plurality of polynucleotides is provided from a theoretical prediction of a dissociation time, $t_{diss}$, for each of the plurality of polynucleotides from a reference probe provided by:

$$t_{diss} = \alpha \exp\left(\beta \frac{\Delta G}{RT}\right)$$

wherein R is the ideal gas constant, T is the temperature in degrees Kelvin, $\Delta G$ is the binding energy and $\alpha$ and $\beta$ are fitting parameters that as fit to experimental data,
wherein the contribution of each of the plurality of polynucleotides to molecules hybridized to the test probe is the contribution of the dissociation profile for each of the plurality of polynucleotides to the dissociation curve.

69. The method of claim 68, wherein the form of the dissociation profile for each of the plurality of polynucleotides is an exponential decay function.

70. The method of claim 63 or 68 wherein said comparing comprises minimizing the value of an objective function of the difference between the dissociation curve and the dissociation profiles.

71. The method of claim 70 wherein the objective function is an absolute square of the difference of the dissociation curve and a combination of the dissociation profiles.

72. The method of claim 71 wherein the combination of the dissociation profiles is a summation of the one or more dissociation profiles.

73. The method of claim 70 wherein the objective function is a $\chi$-squared quantity.

74. The method of claim 25 wherein the reference polynucleotide is cRNA.

75. The method of claim 1, wherein said first solid surface and said second solid surface are the same solid surface.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
                        oligonucleotide

<400> SEQUENCE: 1
ccgcgatacc aattcataga                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
                        oligonucleotide

<400> SEQUENCE: 2
tctatgaatt ggtatcgcgg                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
                        oligonucleotide

<400> SEQUENCE: 3
tctatggatt ggtgtcgcgg                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
                        oligonucleotide

<400> SEQUENCE: 4
gagacagctc ttccgaacat                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
                        oligonucleotide
```

```
<400> SEQUENCE: 5
atgttcggaa gagctgtctc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
                       oligonucleotide

<400> SEQUENCE: 6
atgttcggga gagctgtctc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
                       oligonucleotide

<400> SEQUENCE: 7
atgttcggag aggctgtctc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
                       oligonucleotide

<400> SEQUENCE: 8
atgttgggaa gaggtgtgtg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
                       oligonucleotide

<400> SEQUENCE: 9
ttgttcggtt gtgctgtctc                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
                       oligonucleotide

<400> SEQUENCE: 10
ttgttcggtc gtgctgtctc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
                       oligonucleotide
```

```
<400> SEQUENCE: 11
ttgttcggcc atgctgtctc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
                        oligonucleotide
<400> SEQUENCE: 12
aagaacggaa gagcagacac                                              20
```